(12) United States Patent
Bruder et al.

(10) Patent No.: US 6,819,736 B1
(45) Date of Patent: Nov. 16, 2004

(54) COMPUTED TOMOGRAPHY METHOD AND COMPUTED TOMOGRAPHY APPARATUS

(75) Inventors: Herbert Bruder, Höchstadt (DE); Bernd Ohnesorge, Erlangen (DE); Karl Stierstorfer, Erlangen (DE); Thomas Flohr, Ühlfeld (DE); Stefan Schaller, Fürth (DE)

(73) Assignee: Siemens Aktiengesellschaft, Munich (DE)

( * ) Notice: Subject to any disclaimer, the term of this patent is extended or adjusted under 35 U.S.C. 154(b) by 59 days.

(21) Appl. No.: 10/371,702

(22) Filed: Feb. 20, 2003

(30) Foreign Application Priority Data

Feb. 22, 2002 (DE) .......................................... 102 07 623

(51) Int. Cl.⁷ ................................................. A61B 6/03
(52) U.S. Cl. ............................ 378/15; 378/17; 378/901
(58) Field of Search ............................ 378/4, 8, 15, 17, 378/19, 901

(56) References Cited

U.S. PATENT DOCUMENTS

| | | | |
|---|---|---|---|
| 5,802,134 A | 9/1998 | Larson et al. ................... | 378/4 |
| 6,665,370 B2 * | 12/2003 | Bruder et al. .................. | 378/15 |

FOREIGN PATENT DOCUMENTS

| DE | 198 42 238 A1 | 4/2000 |
|---|---|---|

OTHER PUBLICATIONS

K. Taguchi et al., "Algorithm for Image Reconstruction in Multi–Slice Helical CT," Med. Phys. 25, pp. 550–561, 1998.
H. Hu, "Multi–slice Helical CT: Scan and Reconstruction," Med. Phys. 26, pp. 5–18, 1999.
S. Schaller et al., "New, Efficient Fourier–Reconstruction Method for Approximate Image Recon–Struction in spiral Cone–Beam CT at Small Cone–Angles," SPIE Medical Imaging Conf., Proc. vol. 3032, pp. 213–224, 1997.
S. Schaller et al., "Exact Radon Rebinning Algorithm for the Long Object Problem in Helical Cone–Beam CT," IEEE Transactions on Medical Imaging, vol. 19, No. 5, pp. 361–375, May 2000.

H. Kudo et al., F. Noo and M. Defrise, "Cone–Beam Filtered Back–Projection Algorithm for Truncated Helical Data," in Phys. Med. Biol., 43, pp. 2885–2909, 1998.

* cited by examiner

*Primary Examiner*—David V Bruce
(74) *Attorney, Agent, or Firm*—Brinks Hofer Gilson & Lione

(57) ABSTRACT

The invention relates to a method for performing computer tomography, and to a computed tomography (CT) apparatus, in which a) for scanning an object by a cone-shaped beam exiting from a focal point and by a matrix-like detector array for detecting the beam, the focal point is moved in relation to the object on a spiral path, whose center axis corresponds to a system axis, and the detector array provides output data corresponding to the received radiation; and b) for imaging an object region that executes a periodic motion, a signal that reproduces the course over time of the periodic motion is obtained during the scanning; c) from output data furnished during the motion of the focal point on a spiral segment, images with an inclined image plane are reconstructed, the image planes being inclined relative to the system axis both about a first axis, which perpendicularly intersects the system axis, by an angle of inclination $\gamma$ and about a second axis, which perpendicularly intersects both the first axis and the system axis, by a tilt angle $\delta$; and spiral segments that immediately succeed one another overlap one another by an overlap angle that is greater than or equal to zero; and the spiral segments are selected, taking into account the signal that reproduces the course over time of the periodic motion, such that they correspond to a phase of the periodic motion that is to be imaged.

48 Claims, 12 Drawing Sheets

COMPUTED TOMOGRAPHY METHOD AND COMPUTED TOMOGRAPHY APPARATUS

REFERENCE TO RELATED APPLICATION

The present patent document claims priority to German Application Ser. No. DE 10207623.5, filed Feb. 22, 2002, which is hereby incorporated by reference.

1. Field

The invention relates to a method for performing computer tomography, having the following method steps: for scanning an object by means of a cone-shaped beam exiting from a focal point and by means of a matrix-like detector array for detecting the beam, the focal point is moved in relation to the object on a spiral path about a system axis, and the detector array provides output data corresponding to the received radiation; and from output data furnished during the motion of the focal point on a spiral segment, images of an object region executing a periodic motion are reconstructed, taking into account a signal, obtained in the course of the periodic motion, which reproduces the course over time of the periodic signal. The invention furthermore relates to a computed tomography (CT) apparatus, having a radiation source, from whose focal point a cone-shaped beam is emitted; a matrix-like detector array for detecting the beam, the detector array providing output data corresponding to the received radiation; a device for generating a relative motion between the radiation source and the detector array on the one hand and an object on the other; and an image computer to which the output data is supplied, and a device for creating a relative motion for scanning the object by the beam and the two-dimensional detector array caused by a relative motion of the focal point in respect to a system axis in such a way that the focal point moves on a helical spiral path in relation to the system axis, whose center axis corresponds to the system axis; and where the image computer reconstructs images of an object region executing a periodic motion from output data furnished during the motion of the focal point on a spiral segment while taking a signal into account, which reproduces the course over time of the periodic motion and which was obtained during the scanning process with the aid of an appropriate device.

2. Background

A method and a CT apparatus of this kind are known from DE 198 42 238 A1. This method is disadvantageously suitable only for detector arrays which extend a relatively short distance in the direction of the system axis.

Various CT methods using cone-shaped X-ray beams have become known, in particular in connection with detector arrays having several rows of detector elements. In them, the cone angle that is due to the cone-shaped form of the X-ray beam is taken into account in various ways.

In the simplest case (see, for example, K. Taguchi, H. Aradate in "Algorithm for Image Reconstruction in Multi-Slice Helical CTs", Med. Phys. 25, pp. 550 to 561, 1988, or H. Hu in "Multi-Slice Helical CT: Scan and Reconstruction", Med. Phys. 26, pp. 5 to 18, 1999), the cone angle is ignored, which has the disadvantage that with a large number of rows, and therefore a large cone angle, artifacts appear.

Moreover, the so-called MFR algorithm (S. Schaller, T. Flohr, P. Steffen in "New efficient Fourier reconstruction method for approximate image reconstruction in spiral cone-beam CT at small cone angles", SPIE Medical Imaging Conf. Proc., Vol. 3032, pp. 213 to 224, 1997) has become known, but it is disadvantageous because an elaborate Fourier reconstruction is required, and the image quality leaves something to be desired.

Exact algorithms have furthermore been described (for example by S. Schaller, F. Noo, F. Sauer, K. C. Tam, G. Lauritsch, T. Flohr in "Exact Radon Rebinning Algorithm for the Long Object Problem in Helical Cone-Beam CT", Proc. of the 1999 Int. Meeting on Fully 3D Image Reconstruction, pp. 11 to 14, 1999, or H. Kudo, F. Noo and M. Defrise in "Cone-Beam Filtered Backprojection Algorithm for Truncated Helical Data", Phys. Med. Biol. 43, pp. 2885 to 2909, 1998), which have the disadvantage of an extremely elaborate reconstruction in common.

Another such method and CT apparatus are known from U.S. Pat. No. 5,802,134. In this reference, however, images are reconstructed for image planes which are inclined by an inclination angle $\tau$ about the x-axis relative to the system axis z. By this device, the at least theoretical advantage is achieved that the images contain fewer artifacts if the angle of inclination $\tau$ has been selected to be such that a good adaptation, if possible in accordance with a suitable error criterion, such as the minimum mean square value of the distance of all points of the spiral segment from the image plane, measured in the z-direction, and even an optimal adaptation of the image plane to the spiral path is provided.

In this case, the spiral path of the focal point F illustrated in FIG. 1 is described by the following equations:

$$x_f = -R_f \cos\alpha \quad (1)$$

$$y_f = -R_f \sin\alpha$$

$$z_f = S \cdot p \cdot \frac{\alpha}{2\pi} \text{ or}$$

$$\overline{x}_f = \begin{pmatrix} -R_f \cos\alpha \\ -R_f \sin\alpha \\ Sp\frac{\alpha}{2\pi} \end{pmatrix}$$

In the case where the detector elements of the detector array are arranged in rows extending transversely to the system axis Z and in columns extending parallel to the system axis Z, S stands for the length of one detector row in the direction of the system axis, and p stands for the pitch, where p=h/S, and h stands for the slope of the spiral path per revolution of the focal point F. $\alpha$ is the projection angle, and an image plane will now be addressed that belongs to data that was acquired over a projection angle range of $\pm\alpha$; the reference projection associated with this image plane is at $\alpha_r=0$, and thus represents the center of the projection angle range $\pm\alpha$. Below, $\alpha_r$ will be called the reference projection angle.

In the conventional spiral CT, so-called transverse section images are reconstructed, that is, images for image planes that are perpendicular to the system axis marked z and that thus include both the x-axis and the y-axis; the x- and y-axes are perpendicular to one another and to the system axis z.

In the case of U.S. Pat. No. 5,802,134, conversely, images are reconstructed for image planes that are inclined by an angle of inclination $\gamma$ about the x-axis to the system axis z, as shown in FIG. 2. As a result, the at least theoretical advantage is attained that the images contain fewer artifacts if the angle of inclination $\gamma$ is selected such that there is a good optimal adaptation of the image plane to the spiral path, if at all possible in accordance with a suitable error criterion, such as a minimum mean square value of the distance, measured in the z-direction, of all points in the spiral segment from the image plane.

In the case of U.S. Pat. No. 5,802,134, fan beam data, that is, data acquired using fan beam geometry, which is known per se, and obtained in the motion of the focal point over a spiral segment whose length was 180° plus the fan or cone angle, such as 240°, are used for the reconstruction. Referred to the reference projection angle, $\alpha_r=0$, the applicable equation for the normal vector of the image plane is $$\vec{n}_{ijs}(\gamma) = \begin{pmatrix} 0 \\ -\sin\gamma \\ \cos\gamma \end{pmatrix}.$$

The optimal angle of inclination $\gamma$ is evidently dependent on the slope of the spiral and thus on the pitch p.

In principle, the method known from U.S. Pat. No. 5,802,134 can be employed for arbitrary values of the pitch p. However, below the maximum pitch $p_{max}$, optimal utilization of the available detector area and thus of the radiation dose delivered to the patient to obtain images (detector and hence dose utilization) is not possible, because even though a given transverse slice, that is, a slice of the object that is perpendicular to the system axis a, is scanned over a spiral segment that is longer than 180° plus the fan or cone angle, still in the method known from U.S. Pat. No. 5,802,134, for values of the pitch p below the maximum pitch $p_{max}$, only a spiral segment whose length is 180° plus the cone angle can be used, since using a longer spiral segment would make it impossible to adapt the image plane well enough to the spiral segment.

OBJECT AND SUMMARY

The object is to embody a method and a CT apparatus such that it is also suitable for detector arrays with a great length in the direction of the system axis, and that accordingly makes high-quality images possible. Images with an inclined image plane are reconstructed from output data furnished during the motion of the focal point on a spiral segment; the image planes of these images are inclined relative to the system axis both about a first axis, which perpendicularly intersects the system axis, by an angle of inclination $\gamma$ and about a second axis, which perpendicularly intersects both the first axis and the system axis, by a tilt angle $\delta$.

As a result, even at pitch values that are below the maximum pitch, it is possible to achieve at least approximately complete detector and dose utilization.

Since a signal that reproduces the course over time of the periodic motion is obtained, and the spiral segments are to be selected such that they correspond to a phase of the periodic motion that is to be imaged, the reconstruction of high-quality images is assured, In the simplest case of one variation, the images with an inclined image plane are reconstructed from output data that belong to a spiral segment which originates in a single cycle, i.e., a single period, of the periodic motion.

If the chronological resolution achievable with output data originating in a single cycle of the periodic motion is inadequate, then a variant aspect provides that the images with an inclined image plane from a spiral segment that is composed of output data that originate in a plurality of preferably immediately successive cycles of the periodic motion are reconstructed. In an embodiment, it may be provided that the output data of which the spiral segment is composed originate in subsegments of equal length. For instance, in the case of two subsegments in the first of the two cycles, a subsegment is selected that is in phase with the phase to be imaged of the periodic motion. In the next cycle, a subsegment is determined that is complementary to the first subsegment and, with it, forms a spiral segment, and that has the least possible chronological spacing from the phase to be imaged of the periodic motion.

Alternatively, the output data of which the spiral segment is composed can originate in subsegments of unequal length, each of which is disposed symmetrically to a reference time of the periodic motion. In that case, both subsegments are selected to be in phase with the phase to be imaged of the periodic motion.

To make unambiguous definition of the reference time possible, a variant embodiment provides that this reference time in each case is later than the onset of one period of the periodic motion by a length of time that is equivalent to an adjustable fraction of the period length of the periodic motion. To compensate for fluctuations in the period length, mean period lengths of the periodic motion can be used.

In a first alternative embodiment with regard to the image reconstruction, for a given pitch p and a given z-position $z_{ima}$, output data for a total segment of length $[-\alpha_{max}, +\alpha_{max}]$ are obtained, in which $\alpha_{max}=M\pi/p$, and M is the number of detector rows. This total segment is subdivided into a number $n_{ima}$ of spiral segments that overlap one another, each of which has the length of 180° plus the cone angle. For each of the spiral segments, its own image with an inclined image plane is reconstructed at the point $z_{ima}$. By the reconstruction of an image with an inclined image plane for each of the spiral segments, it is possible, by a suitable choice of the angle of inclination $\gamma$ and the tilt angle $\delta$, to adapt the image plane of the image for each of these spiral segments optimally to the corresponding portion of the spiral segment and to utilize both the detector array and the dose theoretically completely and in practice as nearly completely as possible.

In an alternative second embodiment, on the basis of the output data obtained for a spiral segment, 180° plus the cone angle in length, that is centered relative to the reference projection angle $\alpha_r=0$, a number $n_{ima}$ of images with a variously inclined image plane for various z-positions is reconstructed. By the reconstruction of a plurality of images with a variously inclined image plane for various z-positions, it is possible, by a suitable choice of the angle of inclination $\gamma$ and the tilt angle $\delta$ to adapt the image plane of the image for each of these z-positions optimally to the spiral segment, and to utilize both the detector array and the dose theoretically completely and in practice as nearly completely as possible. In a preferred embodiment, the plurality of inclined image planes intersect on a straight line that extends at a tangent to the spiral.

To obtain the most complete possible detector and dose utilization, in a variant aspect for the extreme values $+\delta_{max}$ and $-\delta_{max}$ of the tilt angle $\delta$ of the inclined image planes belonging to one spiral segment, the following equation applies:

$$\pm\delta_{min} = \arctan\left( \frac{-\frac{SM}{2} + Sp\frac{\alpha_i}{2\pi} \pm RFOV\cos\alpha_i\tan\gamma_0}{-\frac{R_f}{\cos\gamma_0} - (\pm RFOY)\frac{\sin\alpha_i}{\cos\gamma_0}} \right)$$

in which $\gamma_0$ is the value, averaged for the tilt angle $\delta=0$ in accordance with the equation $$\gamma_0 = \tan\left(\frac{-sp\hat{\alpha}}{2\pi R_f \sin\hat{\alpha}}\right)$$

of the angle of inclination $\gamma$.

For the sake of high image quality, in a further variant aspect is provided that for a given amount $|\delta_{max}|$ of the maximum value for the tilt angle $\delta$, the associated optimal value $\gamma_{min}$ of the angle of inclination $\gamma$ is ascertained such that an error criterion, such as a minimum mean square value of the distance, measured in the z-direction, of all the points on the spiral segment from the image plane, is met.

If the axis of rotation about which the focal point rotates about the system axis is not identical to the system axis but instead intersects the system axis at a gantry angle ρ, then for the angle of inclination γ' to be selected, the following equation applies:

$$\gamma' = \arctan \frac{Sp \cdot \cos\rho}{\sqrt{4\pi^2 \cdot R_f + S^2 p^2 + 4\pi \cdot R_f \cos\alpha \sin\rho \cdot Sp}}$$

Once again, for a given amount of the maximum value for the tilt angle $|\delta_{max}|$, the possibility exists of ascertaining the associated optimal value of the angle of inclination γ' such that an error criterion, such as a minimum square value of the distances, measured in the z-direction, of all the points on the spiral segment from the image plane, is met.

To achieve the most complete possible detector and dose utilization, in a variant of embodiment, for the number $n_{ima}$ of inclined image planes for which images with an inclined image plane are generated for each spiral segment, the following equation also applies:

$$n_{ima} = \mathrm{floor}\left[\frac{sM}{p}\right]$$

Also for the sake of the most complete possible detector and dose utilization, on the condition that the detector rows are of equal width, in a variant of the embodiment, the tilt angles δ of the inclined image planes are ascertained in accordance with the equation $$\delta(i) = \delta_{max} \frac{2i - (n_{ima} - 1)}{n_{ima} - 1}$$

To obtain transverse section images, which the users of CT apparatuses are used to, in a variant of the embodiment, reformatting is provided; that is, in a further method act, a transverse section image is generated by combining a plurality of images with an inclined image plane. In one feature, the combining can be done by combining the plurality of images with an inclined image plane into a transverse section image by interpolation, or in particular by weighted averaging.

In combining a plurality of images with an inclined image plane into a transverse section image, it is also possible, in a preferred variant embodiment with a further method act, for the number of images with an inclined image plane that are combined in order to generate a transverse section image to be selected in accordance with whatever slice thickness of the transverse slice is desired. For the sake of the highest possible image quality of the transverse section images, it is also possible for the images with an inclined image plane having the least possible slice thickness to be reconstructed.

A desired slice thickness of the transverse slice represented in a transverse section image can be established, in a further preferred variant, in that the number of images with an inclined image plane that are combined to generate a transverse section image is selected in accordance with the equation $$N_M = 2 \cdot \max(z^*, \sup_\Phi \Delta z_R)/S \cdot N_S$$

The CT apparatus operating as described herein has similar advantages and features as the methods described above. Exemplary embodiments of the invention are described below in conjunction with the drawings.

DESCRIPTION OF THE PREFERRED EMBODIMENTS

Figure 3:
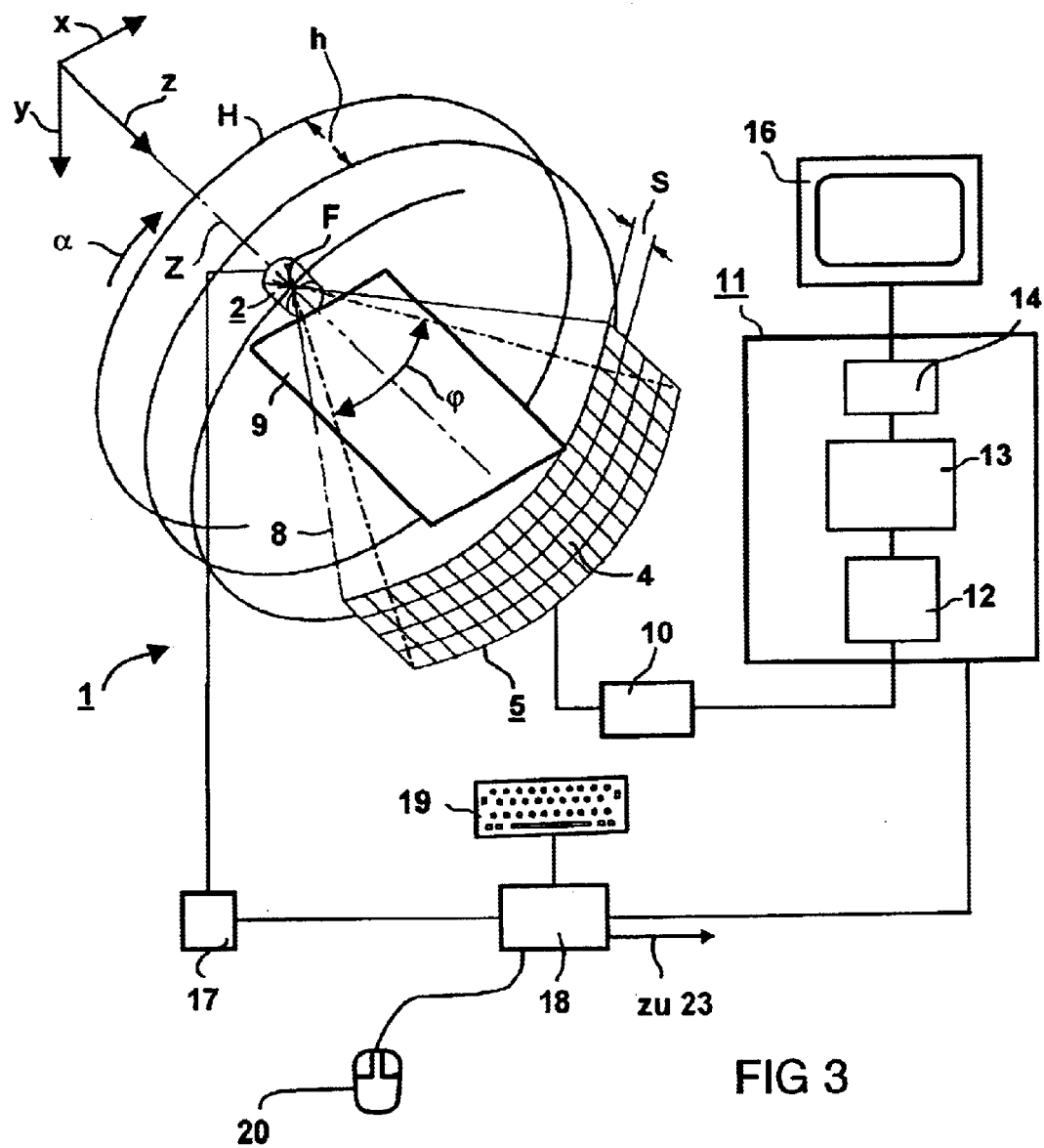
FIGS. 3 and 4 schematically, and partly in the form of block circuit diagrams, show a CT apparatus of one embodiment.
Figure 4:
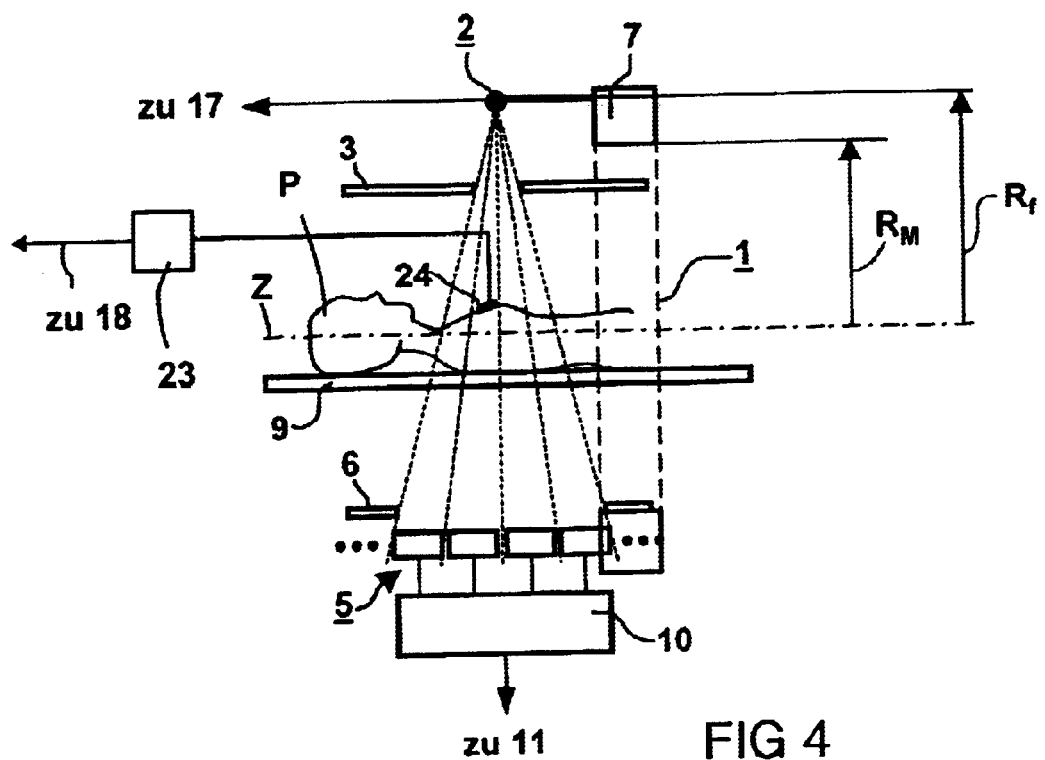

In FIGS. 3 and 4, a third-generation multi-slice CT apparatus according to one embodiment, which is suitable for performing the methods herein, is shown. Its measuring equipment, generally identified by reference numeral 1, has both an x-ray source, generally identified by reference numeral 2, in front of which is a beam aperture 3 (FIG. 4) near the source, and a detector array 5, in front of which is a beam aperture 6 (FIG. 4) near the detector, the detector array 5 being embodied as a large-area array of multiple rows and columns of detector elements—one of which is marked 4 in FIG. 3. The x-ray source 2 with the beam aperture 3 on the one hand and the detector array 5 with the beam aperture 6 on the other are mounted facing one another, as shown in FIG. 4, on a rotating frame 7, hereinafter called a gantry, in such a way that a pyramid-shaped x-ray beam, whose peripheral rays are marked 8 and which originates at the x-ray source 2 in operation of the CT apparatus and are passed through the adjustable beam aperture 3, strikes the detector array 5. The beam aperture 6 is adjusted to suit the cross section, which in turn is adjusted by device of the beam aperture 3, of the x-ray beam in such a way that only the region of the detector array 5 that can be struck directly by the x-ray beam is uncovered. The fact that there are also other rows of detector elements that are covered by the beam aperture 6 is indicated in FIG. 4 by dotted lines.

The x-ray beam has the cone angle f, which is the opening angle of the x-ray beam projected in a plane extending perpendicular to the system axis. The slice thickness f corresponds to the fan angle of the components of the x-ray beam that cooperate with the individual rows of the detector array 6.

The gantry 7 can be set into rotation about a system axis Z by device of a drive mechanism, not shown. The system axis Z is identical to the z-axis of a 3D rectangular coordinate system shown in FIG. 1. The circular opening in the gantry 7 has a radius $R_m$, which is equivalent to the radius of the measurement field or object cylinder. The radius along with the focal spot F moves is designated as $R_f$.

The columns of the detector array 5 also extend in the direction of the z-axis, while the rows, whose width S is measured in the direction of the z-axis and amounts for instance to 1 mm, extend transversely to the system axis Z or z-axis.

To be able to put an object, such as a patient, that is to be examined into the beam path of the x-ray beam, a support device 9 is provided, which is displaceable parallel to the system axis Z, that is, in the direction of the z-axis.

For acquiring volume data of an object being examined, such as a patient, lying on the support device 9, the object being examined is scanned by moving the measuring unit 1 about the system axis Z, creating images of many projections from various projection directions α. The data furnished by the detector array 5 thus contain many projections for each active detector row.

During the continuous rotation of the measuring unit 1 about the system axis Z, the support device 9 is simultaneously displaced continuously in the direction of the system axis Z relative to the measuring unit 1; synchronization between the rotary motion of the rotating frame 7 and the translational motion of the support device 9 exists, in the sense that the ratio of the translational to the rotational speed is constant, and this constant ratio can be set by selecting a value for the advancement h of the support device 9 per revolution of the rotating frame 7 that assures complete scanning of the volume of interest of the object being examined.

The ratio of the advancement h to the width S of one detector row is called the pitch p, as already noted; the maximum pitch $p_{max}$ that still just barely allows gapless scanning of an object being examined is obtained on the condition that all the rows of the detector array 5 have the same width S; the number of active rows of the detector array 5 is n.

Figure 1:
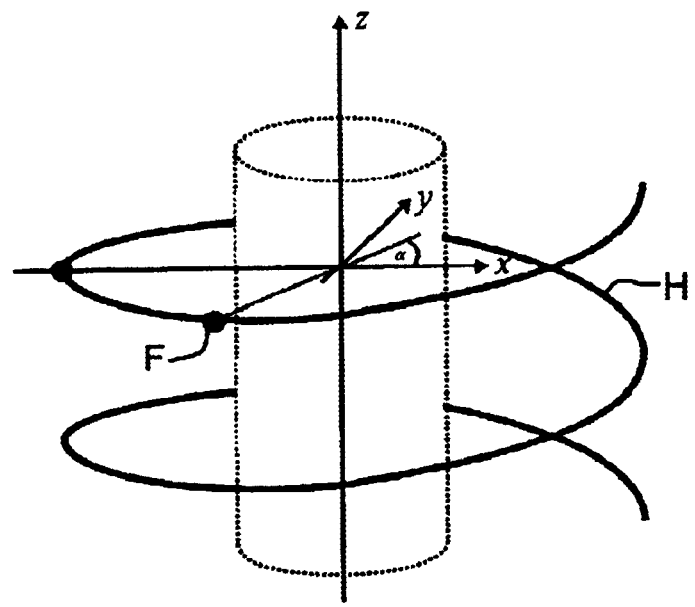
FIGS. 1 and 2 are illustrations of the geometry of methods according to the prior art.

The focal point F of the x-ray source 2 thus moves, from the viewpoint of the object being examined, along a helical spiral path, marked H in FIG. 1, about the system axis Z, which is why the way of picking up volume data is also called spiral scanning. The volume data furnished in this process by the detector elements of each row of the detector array 5, which involves projections that are each associated with a specified row of the detector array 5 and a specified position relative to the system axis Z, are read out in parallel, then serialized in a sequencer 10, and transmitted to an image computer 11.

After preprocessing of the volume data in a preprocessing unit 12 of the image computer 11, the resultant data stream reaches a memory 14, in which the volume data corresponding to the data stream are stored.

The image computer 11 contains a reconstruction unit 13, which from the volume data reconstructs image data, for instance in the form of sectional images of desired slices of the object being examined, by methods known per se to one skilled in the art. The image data reconstructed by the reconstruction unit 13 are stored in a memory 14 and can be displayed on a display unit 16, such as a video monitor, connected to the image computer 11.

The x-ray source 2, such as an x-ray tube, is supplied with the requisite voltages and currents by a generator unit 17. To enable setting it to the various required values, the generator unit 17 is assigned a control unit 18 with a keyboard 19 and a mouse 20, which make the necessary settings possible.

In other respects as well, operating and controlling the CT apparatus is done by the control unit 18, the keyboard 19 and the mouse 20, which is illustrated by the fact that the control unit 18 is connected to the image computer 11.

Figure 2:
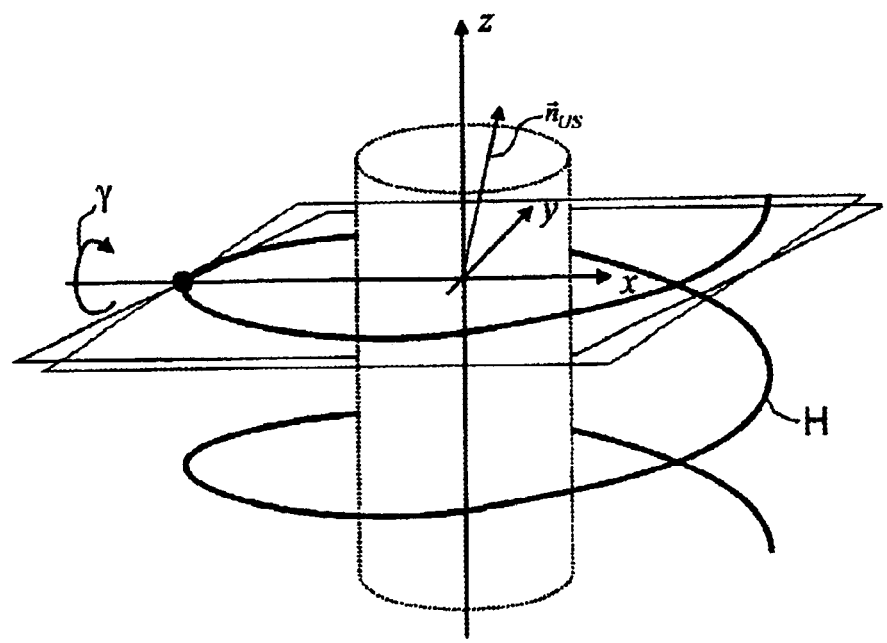

To examine an object region of the patient P that executes a periodic motion, namely to examine his heart, an EKG unit 23 is provided. One of the electrodes connected to the EKG unit 23 is shown in FIG. 2, marked 24. The signal generated by the EKG unit 23 is supplied to the control unit or computer 18, which stores it in memory while the examination is being performed, that is, during a spiral scan of the patient P.

In a first type of operation, which is the usual procedure in spiral scans, transverse section images, which are sectional images those image plane extends perpendicular to the system axis Z, are reconstructed from the volume data picked up in the course of a spiral scan, the reconstruction being done by methods that are known per se and that are called 180 LI reconstruction and 360 LI reconstruction in the literature.

In a second type of operation, however, the possibility also exists, at least as an intermediate step, of reconstructing sectional images from the volume data, the image planes of which images are inclined relative to the system axis Z.

Figure 5:
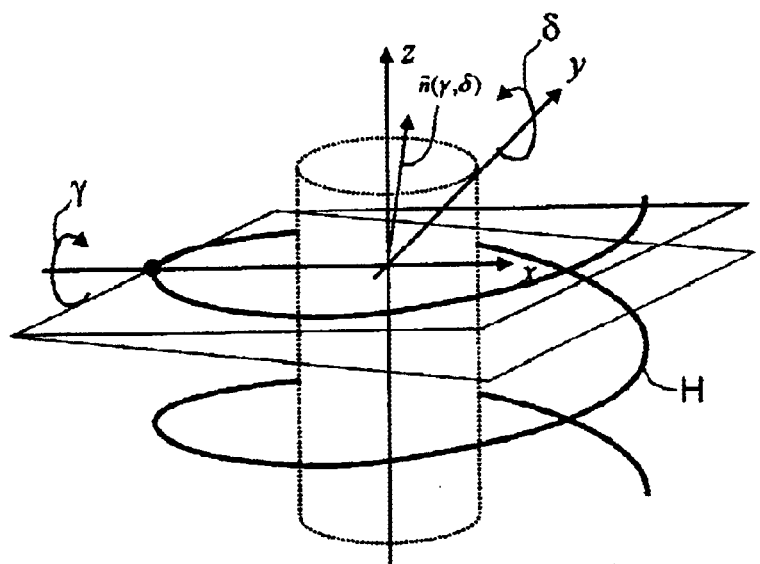
FIG. 5, in a view analogous to FIGS. 1 and 2, is an illustration of the geometry of the method of operation.

Here, in contrast to the procedure known from U.S. Pat. No. 5,802,134, the image plane is inclined relative to the system axis Z both about a first axis, namely the x-axis, intersecting the system axis Z at a right angle, by an angle of inclination γ and the tilt angle δ and about a second axis, namely the y-axis, intersecting both the first axis (x-axis) and the system axis Z at a right angle, by a tilt angle δ, as seen in FIG. 5.

In a first mode of the second type of operation, for a given pitch p and a given z-position, $z_{ima}$, output data are used for a spiral segment of length $[-\alpha_{max}, +\alpha_{max}]$, in which $\alpha_{max}=$ M$\pi$/p, and M is the number of detector rows, and the z-position is the position of the image plane on the z-axis. This total segment is subdivided into a number $n_{ima}$ of spiral segments overlapping one another, each of which has the length of 180° plus the cone angle. For each of the spiral segments, a separate image with an inclined image plane is reconstructed at the location $z_{ima}$. By reconstructing one image with an inclined image plane for each of the spiral segments, it is possible, by a suitable choice of the angle of inclination $\gamma$ and the tilt angle $\delta$, to adapt the image plane of the image for each of these spiral segments optimally to the corresponding section of the spiral path and to achieve theoretically complete, and in practice maximally complete, utilization both of the region of the detector array 4 uncovered by the beam aperture plate 6 and of the radiation dose striking this region.

In an alternative second mode of the second type of operation, a spiral segment 180° plus the cone angle in length that is centered relative to the reference projection angle $\alpha_r=0$ is used, and on the basis of this spiral segment, a number $n_{ima}$ of images with a variously inclined image plane for various z-positions is reconstructed. In this mode as well, it is possible, by the reconstruction of a plurality of images with a variously inclined image plane for various z-positions and by a suitable choice of the angle of inclination $\gamma$ and the tilt angle $\delta$, to adapt the image plane of the image for each of these z-positions optimally to the spiral segment, and to utilize both the detector array and the dose theoretically completely and in practice as nearly completely as possible. In a preferred embodiment, the plurality of inclined image planes intersect on a straight line that extends at a tangent to the spiral.

The second mode will now be described in more detail. For the sake of simplicity, a single spiral segment will be considered, which is centered relative to the reference projection angle $\alpha_r=0$. Since the image planes of the $n_{ima}$ images are inclined both by the angle of inclination $\gamma$ relative to the x-axis and by the tilt angle $\delta$ relative to the y-axis, the normal vector of an image plane is defined by the following equation:

$$\bar{n}(\gamma, \delta) = \begin{pmatrix} \sin\delta \\ -\cos\delta\sin\gamma \\ \cos\delta\cos\gamma \end{pmatrix}. \quad (2)$$

The distance $d(\alpha, \delta, \delta)$ of an arbitrary point $(x_f, y_f, z_f)$ on the spiral path in the z-direction from the image plane inclined by the angle of inclination $\gamma$ and by the tilt angle $\delta$ is defined by the following equation:

$$d(\alpha, \delta, \gamma) = \bar{n}(\gamma, \delta) \cdot \begin{pmatrix} x_f + R_f \\ y_f \\ z_f \end{pmatrix} = \bar{n}(\gamma, \delta) \cdot \begin{pmatrix} -R_f\cos\alpha + R_f \\ -R_f\sin\alpha \\ Sp\dfrac{\alpha}{2\pi} \end{pmatrix} \quad (3)$$

$$= R_f(1-\cos\alpha)\sin\delta + R_f\sin\alpha\cos\delta\sin\gamma + Sp\dfrac{\alpha}{2\pi}\cos\delta\cos\gamma$$

It is assumed here that the position $(-R_f,0,0)$ of the focal point F for the reference projection angle $\alpha_r=0$ is located in the image plane.

The angle of inclination $\gamma$ and the tilt angle $\delta$ of the inclined image plane are selected such that the mean square value of all the points on the spiral segment is minimal.

If b-t is defined as the coordinate system x-y that is rotated by an angle a-$\pi$/2, then b-t is the local coordinate system for a projection at a projection angle $\alpha$.

$x = b \sin \alpha + t \cos \alpha$ $y = -b \cos \alpha + t \sin \alpha \quad (4)$ If one imagines a virtual detector array that corresponds to the projection of the detector array in a plane that contains the system axis z, or so-called virtual detector plane, then for the detector plane, t=0.

Each point (x, y, z) on the image plane is defined by the following equation:

$$\bar{n}(\gamma, \delta) \cdot \begin{pmatrix} x+R_f \\ y \\ z \end{pmatrix} = (x+R_f)\sin\delta - y\cos\delta\sin\gamma + z\cos\delta\cos\gamma = 0 \quad (5)$$

If equation (4) where t=0 is inserted into equation (5), the result is the straight-line intersection of the virtual detector plane with the image plane:

$$z(b) = -R_f\dfrac{\tan\delta}{\cos\gamma} - b\left(\sin\alpha\dfrac{\tan\delta}{\cos\gamma} + \cos\alpha\tan\gamma\right). \quad (6)$$

The z-coordinate on the virtual detector plane is defined by $$z_{Det}(b) = z(b) - Sp\dfrac{\alpha}{2\pi} \quad (7)$$

$$= -R_f\dfrac{\tan\delta}{\cos\gamma} - Sp\dfrac{\alpha}{2\pi} - b\left(\sin\alpha\dfrac{\tan\delta}{\cos\gamma} + \cos\alpha\tan\gamma\right).$$

The angle of inclination $\gamma$ is first optimized, in the same way as in U.S. Pat. No. 5,802,134, that is, for the tilt angle $\delta=0$. The result obtained is $$\tan\gamma_0 = \dfrac{-Sp\hat{\alpha}}{2\pi R_f \sin\hat{\alpha}}, \quad (8)$$

in which $\hat{\alpha}$ is the angle at which the spiral path pierces the image plane. It has been demonstrated that $\hat{\alpha}=\pi/3$ is a favorable, if not optimal, value for this parameter.

For the angle of inclination $\gamma$ obtained with equation (8), using $\hat{\alpha}=\pi/3$, the tilt angle $\delta$ is optimized. The criterion for optimization of the tilt angle $\delta$ is that the z-coordinate of equation (7) for the lines=RFOV$\leq$b$\leq$RFOV, by which lines the region of the object being examined and reached by the radiation is defined in the z-direction to the rear and to the front, respectively, is not only located only inside the active detector area, that is, within the region of the detector array 5 uncovered by the beam aperture plate and struck by the radiation, but also utilizes the detector area as well as possible.

For the maximum possible tilt angle $\pm\delta_{max}$, the lines defined by the z-coordinate of equation (7), where b=$\pm$RFOV, reach the front and rear ends, respectively, of the detector area in the z-direction. If for the applicable spiral segment of the projections this condition ensues at the beginning and end of the spiral segment, that is, for the outermost projection angles $\alpha_1=\pm120°$, then the following equation applies:

$$z_{Det}(b = \pm RFOV) = \pm \frac{SM}{2}, \quad (9)$$

in which M is the number of detector rows, and S is the width of one detector row, measured in the z-direction.

Inserting equation (b) for $\alpha=\alpha_1$ and $\gamma=\gamma_0$ and solving for $\delta_{max}$, the results are:

$$\tan\delta_{max} = \frac{-\frac{SM}{2} + Sp\frac{\alpha_1}{2\pi} \pm RFOV\cos\alpha_1\tan\gamma_0}{-\frac{R}{\cos\gamma_0} - (\pm RFOV)\frac{\sin\alpha_1}{\cos\gamma_0}} \quad (10)$$

bzw.

$$\pm\delta_{max} = \arctan\left(\frac{-\frac{SM}{2} + Sp\frac{\alpha_1}{2\pi} \pm RFOV\cos\alpha_1\tan\gamma_0}{-\frac{R_f}{\cos\gamma_0} - (\pm RFOV)\frac{\sin\alpha_1}{\cos\gamma_0}}\right)$$

For the corresponding $\delta_{max}$, a new $\gamma_{min}$ is ascertained by reiteration, specifically by minimizing the mean square value of the distances $d(\alpha, \delta_{max}, \gamma)$ measured in the z-direction of all the points on the spiral segment from the image plane in accordance with equation (3).

The available range $[-\delta_{max}, \delta_{max}]$ of the tilt angle is now preferably subdivided in accordance with the number $n_{ima}$ of images with an inclined image plane that are to be reconstructed, as in the case of the exemplary embodiment described. That is, with a uniform subdivision, each image plane $0 \leq i \leq n_{ima}-1$ is defined by the angle of inclination $\gamma_{min}$ (which is preferably the same for all image planes, as in the exemplary embodiment described) and by the applicable tilt angle $\delta_{(i)}$, for which angle the applicable equation is $$\delta(i) = \delta_{max}\frac{2i - (n_{ima} - 1)}{n_{ima} - 1}. \quad (11)$$

The number $n_{ima}$ of images with inclined image planes to be reconstructed for the spiral segment is defined by $$n_{ima} = \text{floor}\left[\frac{sM}{p}\right]. \quad (12)$$

The method and CT apparatus will now be described, taking as an example a CT apparatus with M=12 detector rows of width S, which is operated with a pitch of p=12. For each z-position $z_{ima}$, a spiral segment $[-\alpha_{max}, \alpha_{max}]$ in length, with $\alpha_{max}=\pi$, is plotted.

Figure 6:
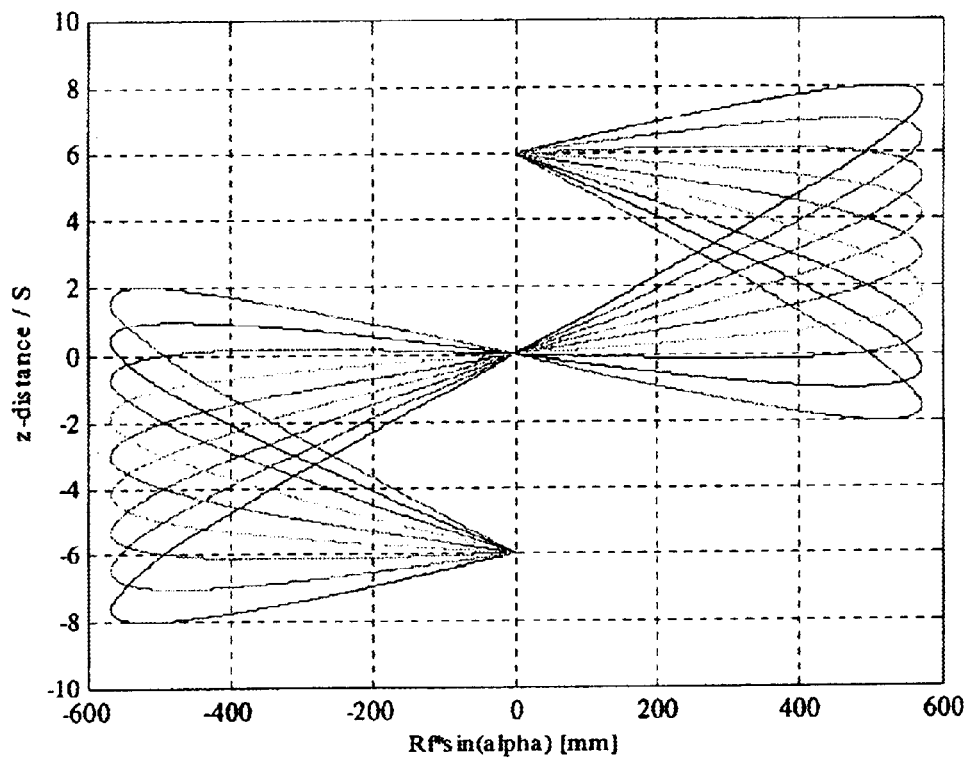
FIG. 6 shows the distances, referred to the width S of one row of the detector and measured in the direction of the z-axis, of all the points in one spiral segment from the image plane for various angle of inclinations γ, plotted over the sine, multiplied by the radius $R_f$, of the projection angle α, specifically for the tilt angle δ=0.

In FIG. 6, the distances of all the points of this spiral segment from the image plane, measured in the direction of the z-axis and referred to the width S of one row of the detector array, are plotted for various angle of inclinations $\gamma$ over the sine, multiplied by the radius $R_f$, of the projection angle $\alpha$, specifically for the tilt angle $\gamma=0$.

Figure 7:
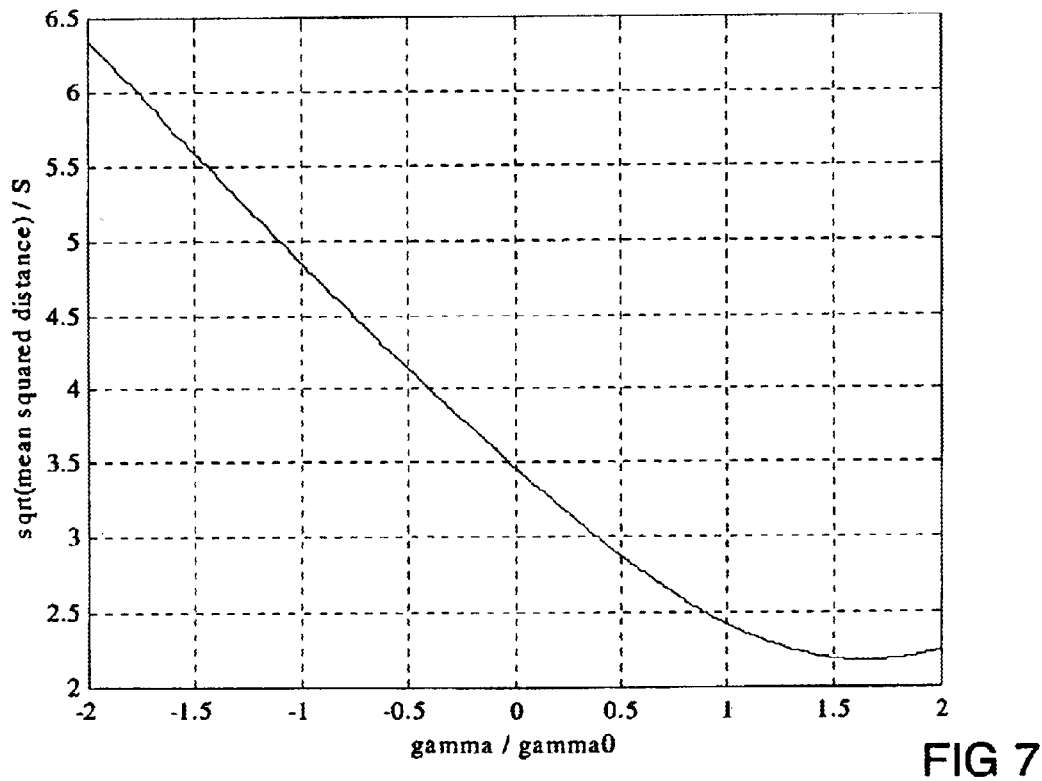
FIG. 7 shows the square roots of the mean square values, referred to the width S of one detector row and plotted over the quotient $\gamma/\delta_0$, of the distances of all the points on the spiral segment in question from the image plane, the distances being measured in the direction of the z-axis.

FIG. 7, based on FIG. 6 and on the assumption that the spiral segment in question contributes in its entirety to the applicable image, shows the square roots, plotted over the quotient $\gamma/\gamma_0$ and referred to the width S of one detector row, of the mean square values of the distances, measured in the direction of the z-axis, of all the points on the spiral segment in question from the image plane, which will hereinafter be called the SMSD (square root mean square distance).

It is clear from FIG. 7 that by optimizing $\gamma$, the SMSD is reduced from 3.5 S, for the case of an image plane that is completely uninclined, so that $\gamma=0$, to 2.2 S. It is assumed here that the improvement in image quality that can be attained by the method of U.S. Pat. No. 5,802,134 can be ascribed to this reduction in the SMSD. Moreover, the value of the angle of inclination $\gamma$ for which SMSD is minimal, for the value in question of the pitch p, differs only insignificantly from the value of $\gamma_0$ ascertained by equation (8).

If instead of a single image for the entire spiral segment, the number $n_{ima}$, required by equation (12), of images with an inclined image plane are reconstructed, the result, for the values selected for the present example of M=12 and p=12, is a number $n_{ima}=2$. In other words, for a total segment of length $2\alpha_{max}=2\pi=360°$, for two spiral segments of length 180° plus the cone angle, i.e. the length 240° for example, which are offset from one another by 120° and thus together include the total segment, two images with an inclined image plane are each reconstructed. The image planes of the images have different z-positions, and thus according to equation (11) they have different tilt angles $\delta$, namely $-\delta_{max}$ and $\delta_{max}$.

Figure 8:
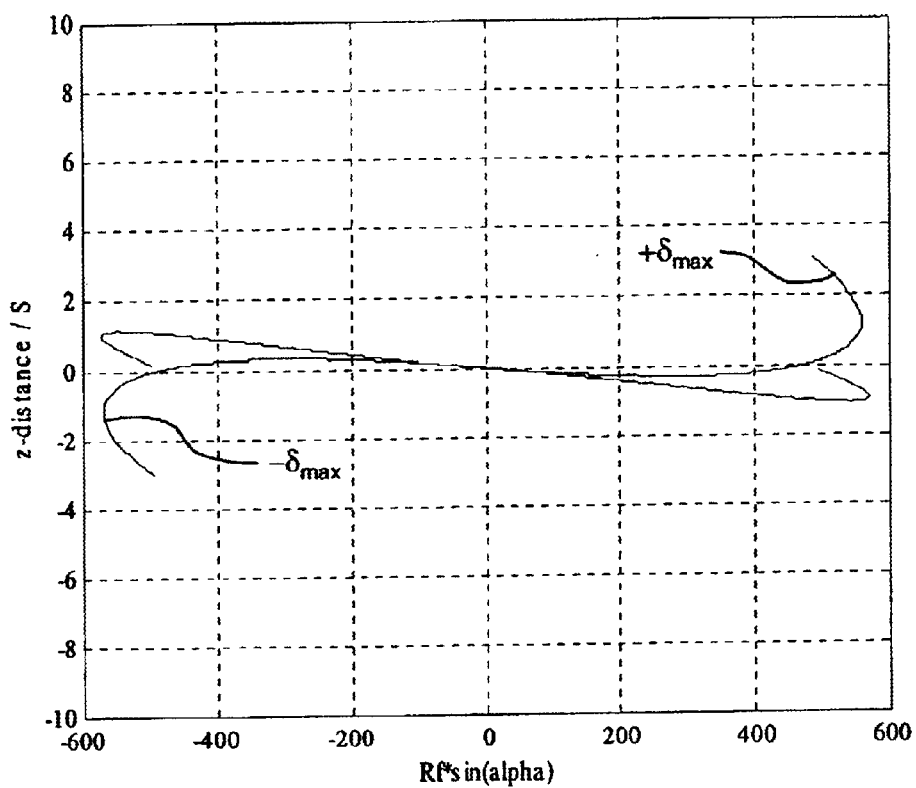
FIG. 8, for one spiral segment, shows the distances, referred to the width S of one row of detector elements and measured in the direction of the z-axis, of all the points on the spiral segment from the image planes, inclined by both $-\delta_{max}$ and $+\delta_{max}$ as well as by $\gamma_{min}$, of the two images belonging to this spiral segment, plotted over the sine, multiplied by the radius $R_f$, of the projection angle α.

In FIG. 8, for one of the spiral segments 240° in length, the distances, referred to the width S of one row of detector elements and measured in the direction of the z-axis, of all the points on this spiral segment from the image planes, inclined by $-\delta_{max}$ and $+\delta_{max}$ and each by $\gamma_{min}$, of the two images belonging to this spiral segment are plotted over the sine, multiplied by the radius $R_f$, of the projection angle $\alpha$. First, $\delta_{max}$ and $\gamma_0$ are ascertained on the basis of equations (8) and (10); for the sake of optimization, a reiteration of the angle of inclination $\gamma$ is then performed on the basis of $\delta_{max}$, for which purpose SMSD is ascertained separately for the two image planes of the spiral segments in question, and then a total SMSD is formed as a square root of the separately ascertained SMSDs, and finally the angle of inclination $\gamma$ is reiterated, which leads to $\gamma_{min}=1.26\cdot\gamma_0$, and to an SMSD that is a total of 0.8 S.

Compared to the method known from U.S. Pat. No. 5,802,134—tilt angle where $\delta=0$ and with reconstruction of a single image from the total segment—this is about a reduction in SMSD by a factor of more than 3, and it promises an improvement in image quality.

Figure 9:
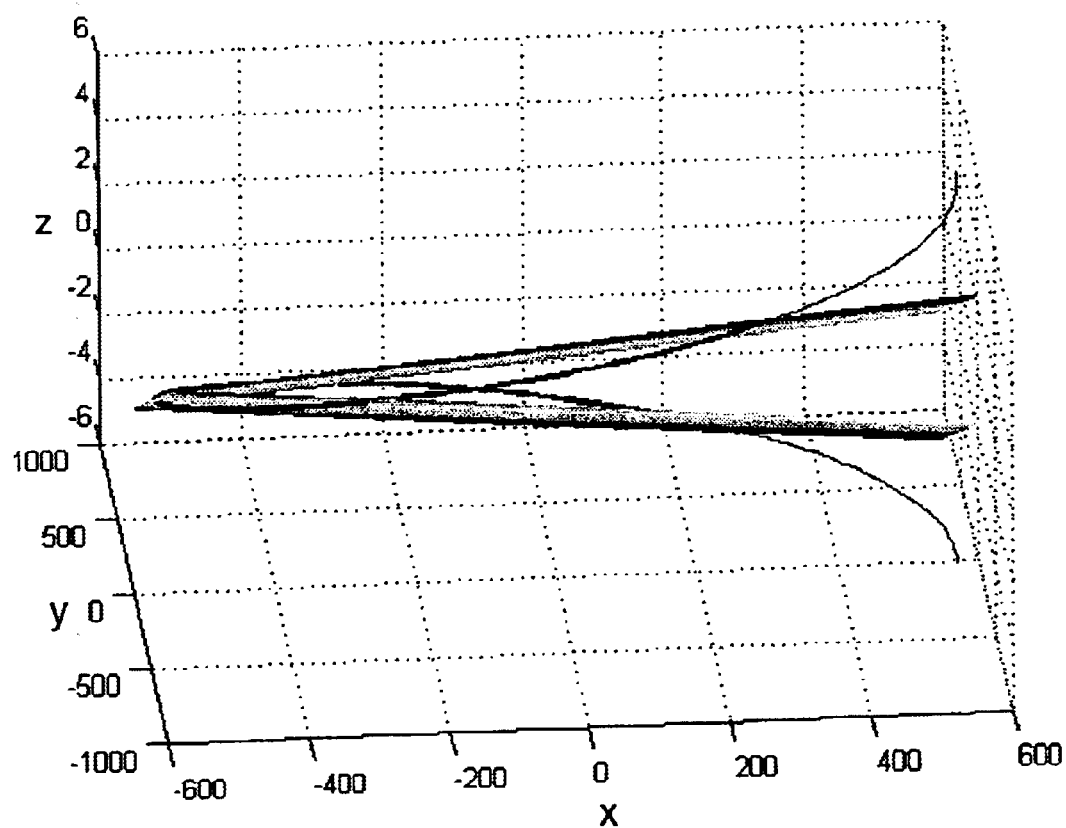
FIGS. 9 and 10 show the image planes belonging to one spiral segment, in perspective viewed from different angles.
Figure 10:
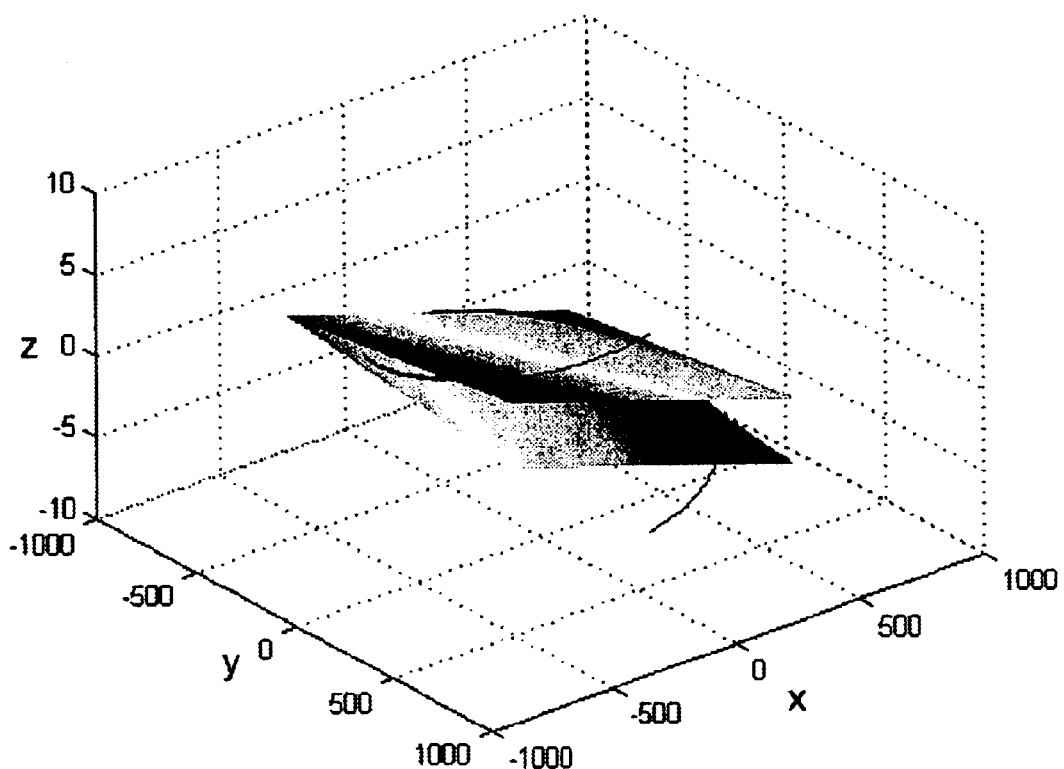

The image planes belonging to one of the two spiral segments, each of 240° in length, are shown as examples in FIGS. 9 and 10 in perspective from different angles. It can be seen particularly from FIG. 10 that the two inclined image planes intersect at a straight line extending at a tangent to the spiral, as noted.

Figure 11:
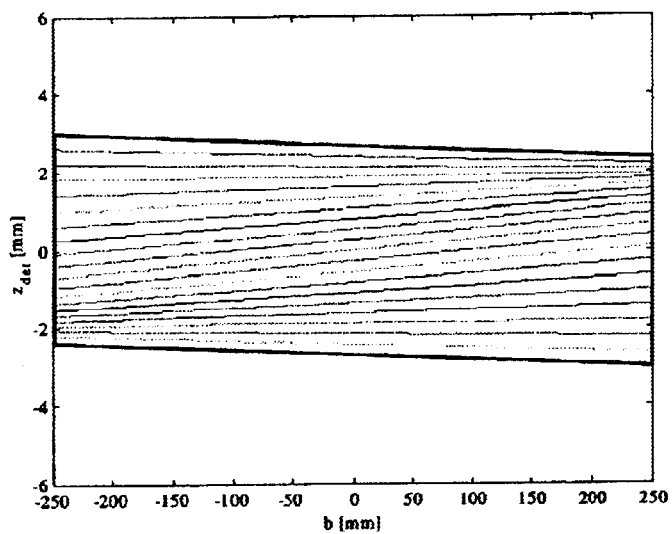
FIG. 11 illustrates the detector utilization and hence the dose utilization for a CT apparatus of the prior art, in terms of the virtual detector, where M=12 and p=8.

The detector utilization and thus dose utilization for the method known from U.S. Pat. No. 5,802,134 is shown in FIG. 11 in terms of the virtual detector, where M=12 and p=8. The region outlined by the heavy parallelogram-shaped line indicates the region of the virtual detector area onto which the inclined image plane belonging to the spiral segment is projected during the motion of the focal point along the spiral segment.

It becomes clear that large portions of the detector area remain unused, and correspondingly the dose utilization is also low. A theoretically optimal detector and dose utilization is possible only for the maximum pitch $p_{max}=12$. As the pitch p decreases, the detector and dose utilization become worse and worse.

Figure 12:
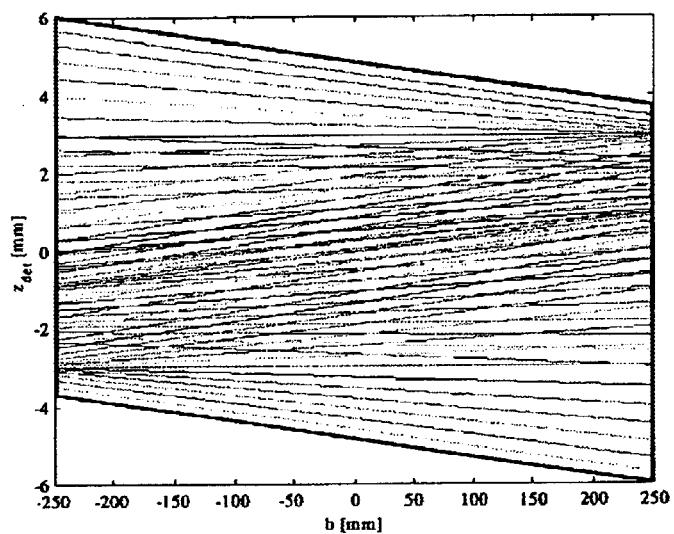
FIGS. 12 and 13 illustrate the detector utilization and hence the dose utilization for a CT apparatus of one embodiment, in terms of the virtual detector, where once again M=12 and p=8.

For the embodiments herein, the detector and hence dose utilization is shown in FIG. 12 in terms of the virtual detector, again with M=12 and p=8. The region outlined by the heavy parallelogram-shaped line indicates the region of the virtual detector area onto which the number $n_{ima}=3$ of inclined image planes belonging to the spiral segment in accordance with equation (12) are projected during the motion of the focal point along the spiral segment.

The great majority of the virtual detector area is utilized—only two small triangular regions remain unused—and the dose utilization is correspondingly high as well.

Figure 13:
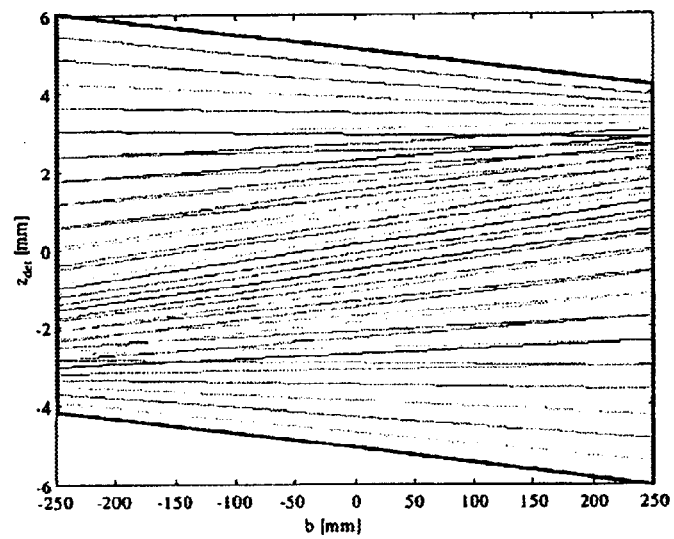

FIG. 13 analogously to FIG. 12 shows the conditions where M=12 and p=12. Accordingly, the region outlined by the heavy parallelogram-shaped line again indicates the region of the virtual detector area onto which the number $n_{ima}=2$ of inclined image planes belonging to the spiral segment in accordance with equation (12) are projected during the motion of the focal point along the spiral segment.

As the comparison of FIGS. 11 and 12 shows, in practice there is an only slight dependency of the detector and dose utilization on the pitch p; that is, the two small unused triangular regions of virtual detector area gradually grow as the pitch p decreases.

Accordingly it becomes clear that in contrast to the method known from U.S. Pat. No. 5,802,134, the detector and hence the dose utilization is largely independent of the pitch p and is virtually optimal.

These embodiments are also significant for examinations of the heart.

Figure 14:
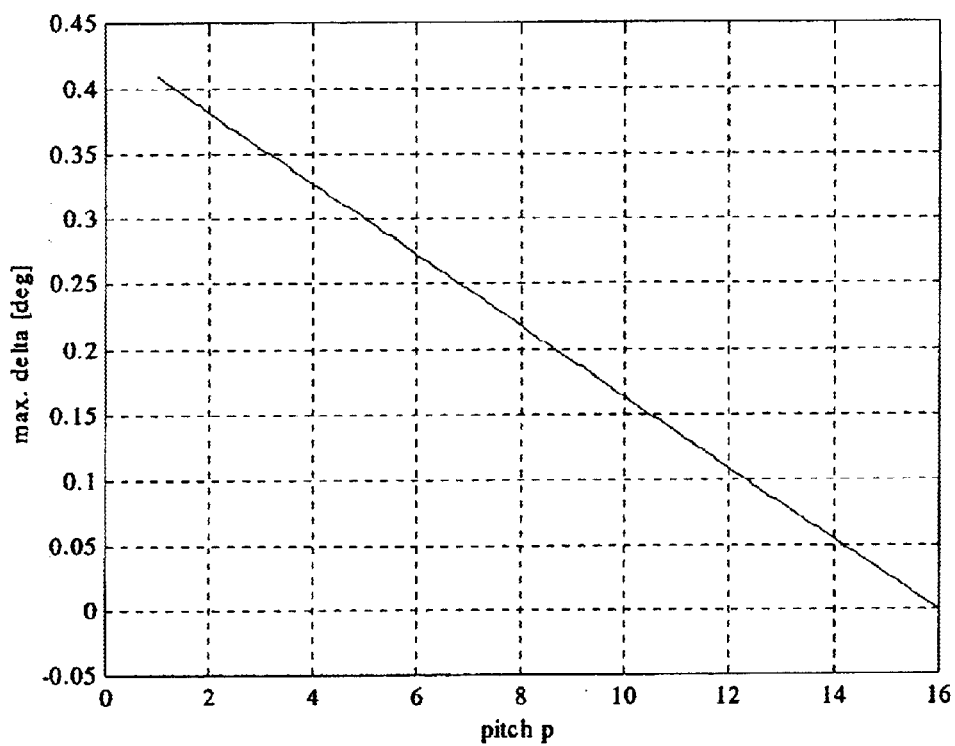
FIG. 14 shows the maximum tilt angle $\gamma_{max}$ as a function of the pitch p when M=12.

FIG. 14 shows the maximum tilt angle $\delta_{max}$, ascertained according to equation (10), as a function of the pitch p for a CT apparatus where M=12. It can be seen that where p=16 and $\delta_{max}=0$, the process changes over to the algorithm known from U.S. Pat. No. 5,802,134 the disclosure of which is incorporated herein by reference.

By using the equation $$\Delta z = R_f \tan \delta_{max} \qquad (13)$$

the tilt angle $\delta$ can be transformed into a z-displacement of the corresponding image.

This is similar to a displacement of the reference projection angle $\alpha_r$ of $$\Delta \alpha = R_f \tan \delta_{max} \frac{2\pi}{pS} \qquad (14)$$

Accordingly, at an arbitrary z-position, images of spiral segments 240° in length can be calculated, which are centered in a region of $[-\Delta\alpha, \Delta\alpha]$ of reference projection angles.

Figure 15:
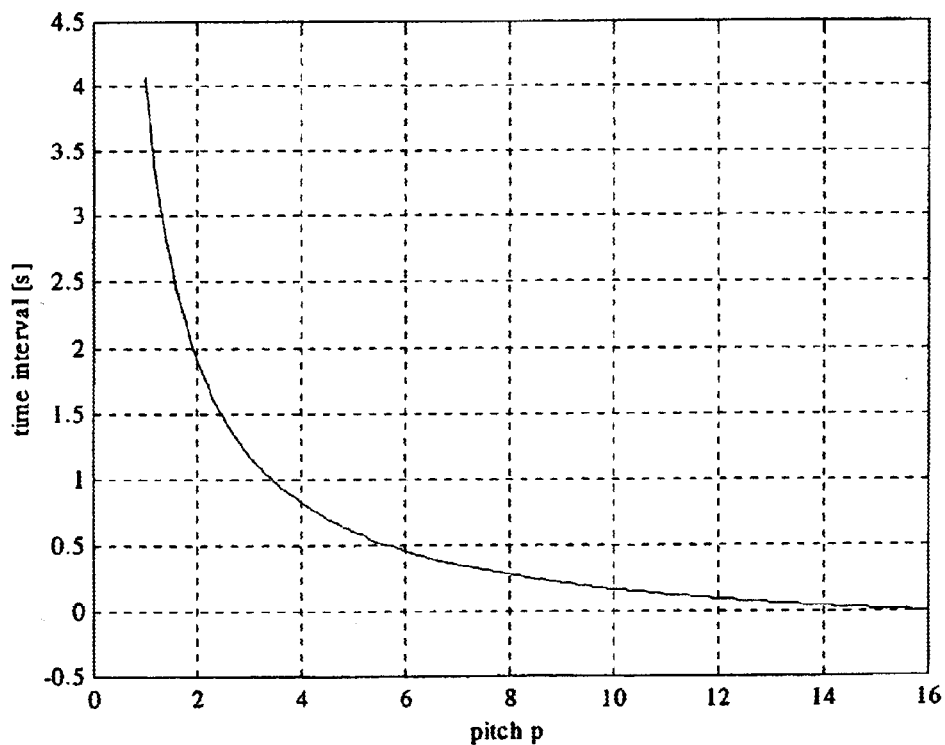
FIG. 15 shows the covered time interval for an arbitrary z-position as a function of the pitch p where $T_{rot}$=0.5 s.

If one revolution of the gantry takes place in the time $T_{rot}$, this region corresponds to a time interval $[-\Delta\alpha, \Delta\alpha] \cdot T_{rot}/2\pi$ in length. If $T_{rot}=0.5$ s, the time interval covered for an arbitrary z-position is shown in FIG. 15 as a function of the pitch p.

If a spiral segment 240° length is to fit in its entirety on the virtual detector area in every case, then a maximum pitch of p=3 is available, in order to cover a time interval of one second, which is equivalent to one complete cardiac cycle, at a pulse rate of 60 beats per minute (60 bpm).

Figure 16:
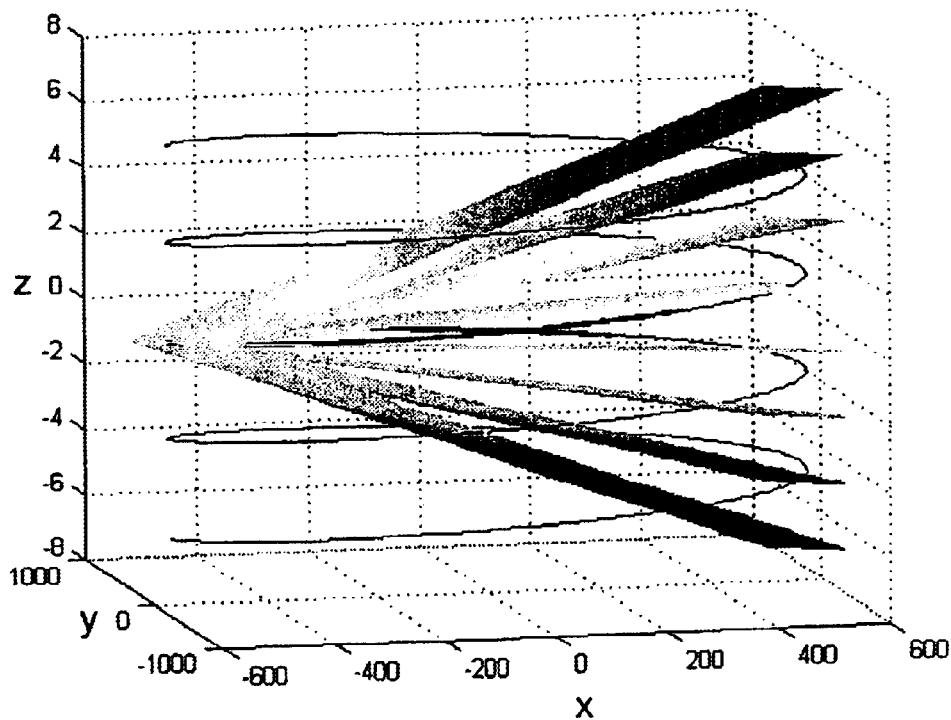
FIG. 16 shows the image planes of the images that are obtained for the same reference projection angle $\alpha_r$, that is, from the same cardiac cycle, and specifically where M=12 and p=3.

The image planes of the images that are obtained for the same reference projection angle $\alpha_r$, that is, from the same cardiac cycle, are shown in FIG. 16. To obtain transverse section images, reformatting is necessary. The entirety of the inclined image plane of images belonging to one reference projection angle will hereinafter, for the sake of simplicity, be called a booklet. The individual images with an inclined image plane in one booklet are hereinafter also called pages for the sake of simplicity, and the number of pages is $N_{tilt}$.

As noted, reformatting is used if transverse section images are to be obtained; in conventional CT apparatuses, this may not be done.

The currently available multi-slice CT apparatuses have a few rows of detector elements, for instance four rows. For this number of rows, the oblique beam course of the x-rays can be ignored. For such CT apparatuses, conventional algorithms for reconstructing transverse section images from spiral data have therefore been expanded. Once a spiral weighting with a suitable weighting function has been performed for defining the reconstruction slice thickness, a single-row data set is on hand, from which a transverse section image is reconstructed using a convolution-back projection algorithm. The reconstruction slice thickness, that is, the thickness of the slice, detected in the reconstructed transverse section image, of the object being examined is defined by the choice of the width of the weighting function used in the spiral weighting. It is possible to vary the reconstruction slice thickness only by device of another reconstruction with a changed weighting function.

For CT apparatuses with not too high a number of rows ($M \leq 40$), an adaptation to the oblique beam course of the x-radiation is accomplished in the reconstruction, in that as already explained, images for image planes that are adapted in their inclination to the spiral scanning geometry are reconstructed. Because of the inclination of the image planes, after the reconstruction, a recalculation, hereinafter called reformatting, of these images with image planes inclined relative to the system axis into transverse section images, is used. If this is not done, then in secondary views of a reconstructed image volume in particular (for instance, sagittal or coronal views), geometric relationships is to be expected.

The reformatting is done with the aid of interpolation functions of selectable width; as a result, influence can be exerted on the slice sensitivity profile and the image noise in the resultant transverse section.

It is advantageous that the definition of the desired reconstruction slice thickness is done retrospectively in the course of the reformatting.

The requisite number of images with an inclined image plane for the reformatting to be performed in order to obtain a transverse section image at the z-position $z=z_R$ is obtained as follows:

At the periphery of the object cylinder, parameterized by device of $(x,y)=(R_M \cos(\Phi), R_M \sin(\Phi))$, the distance $\Delta z_R$ of an image plane, inclined by the angle of inclination and the tilt angle, is obtained, with the normal vector:

$$\vec{n}(\gamma, \delta) = \begin{pmatrix} \sin\delta \\ -\cos\delta\sin\gamma \\ \cos\delta\cos\gamma \end{pmatrix}.$$

and with the zero point at the point $(-R_f, 0, z_R)$, by inserting $(x, y, \Delta z_R)$ into the equation of the planes:

$$\vec{n}(\delta, \gamma) \cdot \vec{x} = 0.$$

It then follows that:

$$\Delta z_R = -\frac{\tan(\delta)}{\cos(\gamma)} \cdot (-R_f + R_M \cdot \cos(\Phi)) + \tan(\gamma) \cdot R_M \cdot \sin(\Phi). \qquad (15)$$

For reformatting a transverse section image with the image plane at $z_R$, accordingly all the images with an inclined image plane that are reconstructed in the interval $$[((z_R - \sup_\Phi \Delta z_R(\Phi, \delta))), ((z_R + \sup_{101} \Delta z_R(\Phi, \delta)))] \qquad (16)$$

are accordingly available, or in other words stored in the memory 14.

If in the reformatting an interpolation function is used whose length z* exceeds the limit values set by the above interval, then the number of reconstructed images with an inclined image plane required for the reformatting is determined by the length of the interpolation filter.

In the general case, for the number $N_M$ of the reconstructed images with an inclined image plane that are required for reformatting one transverse section image, the applicable equation is:

$$N_M = 2 \cdot {}_{max}(z^*, \sup_\Phi \Delta z_R)/S \cdot N_s \qquad (17)$$

In this equation, $N_s$ is the number of images with an inclined image plane reconstructed per width S of one row of detector elements.

For instance, for a detector array with sixteen rows of detector elements, for a pitch p=16 and with the number $N_S=4$ of images with an inclined image plane reconstructed per width S, what one obtains as the number $N_M$ of the reconstructed images with an inclined image plane required to reformat one transverse section image is $N_M=10$, specifically on the precondition that a triangular interpolation function of the half-value width S is used.

Because of the fact that the reconstruction slice thickness of a desired transverse section image is defined retrospectively, the reconstruction of the images with an inclined image plane is preferably done by the choice of a suitably narrow weighting function in the spiral reconstruction with the smallest possible reconstruction slice thickness. This assures maximum resolution in the z-direction, not only of the images with inclined image planes but also of the transverse section image obtained by the reformatting.

Besides this advantage, the following further advantages of the reformatting described can be named:

- the reconstruction slice thickness can be selected retrospectively, without requiring a new reconstruction;
- the reconstruction slice thickness can be selected freely; and
- for the reformatting, many suitable interpolation functions of freely selectable width are available.

Figure 17:
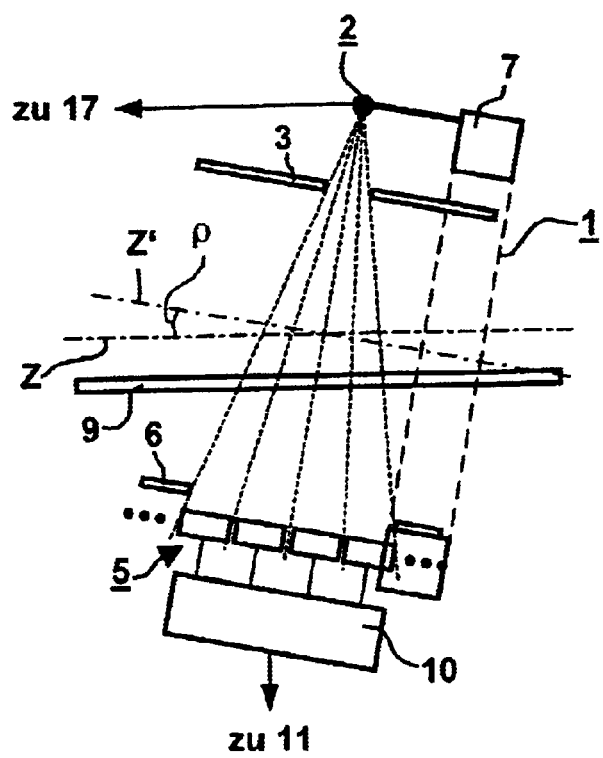
FIG. 17, in a view similar to FIG. 4, shows the CT apparatus of one embodiment in an operating state with the gantry inclined relative to the system axis.
Figure 18:
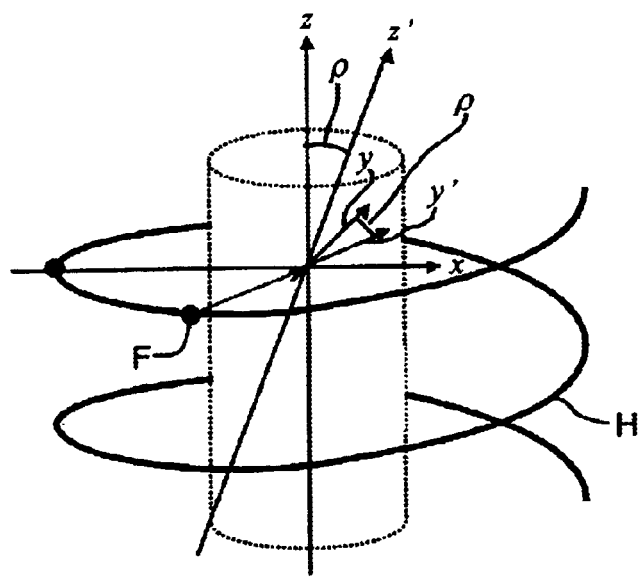
FIG. 18, in a view similar to FIG. 1, shows the geometry of the CT apparatus of one embodiment in the operating state as in FIG. 17, with the gantry inclined relative to the system axis.

In the mode of operation shown in FIG. 17, with an inclined gantry 7, if the axis of rotation $Z^t$ about which the focal point F rotates about the system axis Z is not identical to the system axis Z, but instead intersects it at a so-called gantry angle ρ, the result of the geometry in FIG. 5 is a coordinate system, tilted as shown in FIG. 18, in which the $z^t$-axis, corresponding to the center axis of the spiral path H, is tilted by the gantry angle ρ relative to the z-axis; the $y^t$-axis is likewise tilted by the gantry angle ρ relative to the y-axis; and the x-axis is maintained unchanged.

In this coordinate system, the following equation is true for the spiral path H:

$$\bar{x}'_f = \begin{pmatrix} -R_f \cos\alpha \\ -R_f \sin\alpha + Sp\frac{\alpha \sin\rho}{2\pi} \\ Sp\frac{\alpha \cos\rho}{2\pi} \end{pmatrix} \quad (18)$$

The procedure described above for determining the maximum tilt angle $\delta_{max}$ can be adopted to the case with the tilted gantry, in which case, instead of equation (7), the following applies:

$$z'_{Det}(b) = z'(b) - Sp\frac{\alpha \cos\rho}{2\pi} = -R_f \frac{\tan\delta}{\cos\gamma} - Sp\frac{\alpha \cos\alpha}{2\pi} - b\left(\sin\alpha\frac{\tan\delta}{\cos\gamma} + \cos\alpha\tan\gamma\right), \quad (19)$$

from which, where b=±RFOV, the result is $$z'_{Det}(b = \pm RFOV) = \pm\frac{SM}{2}\sqrt{1 - \left(\frac{b}{R_f}\right)^2} + a\sin\frac{b}{R_f} Sp\frac{\cos\alpha}{2\pi} \quad (20)$$

However, then the angle of inclination γ' in the coordinate system (x,y',z') must be inserted into the determining equation for the maximum tilt angle $\delta_{max}$, that is, into equation (10), for the case with the inclined gantry.

For the angle of inclination γ' in the case of the inclined gantry, the following equations apply:

$$\tan\gamma' = \partial z \frac{\partial z'}{\partial s} = \frac{\partial z'}{\partial \alpha} \cdot \frac{\partial \alpha}{\partial s} \quad (21)$$

$$= \frac{Sp \cdot \cos\rho}{\sqrt{4\pi^2 \cdot R_f + S^2 p^2 + 4\pi \cdot R_f \cos\alpha \sin\rho \cdot Sp}}$$

bzw.

$$\gamma' = \arctan\frac{Sp \cdot \cos\rho}{\sqrt{4\pi^2 \cdot R_f + S^2 p^2 + 4\pi \cdot R_f \cos\alpha \sin\rho \cdot Sp}}$$

in which s is the length of the curve of the spiral path H for the particular spiral segment in question.

Figure 19:
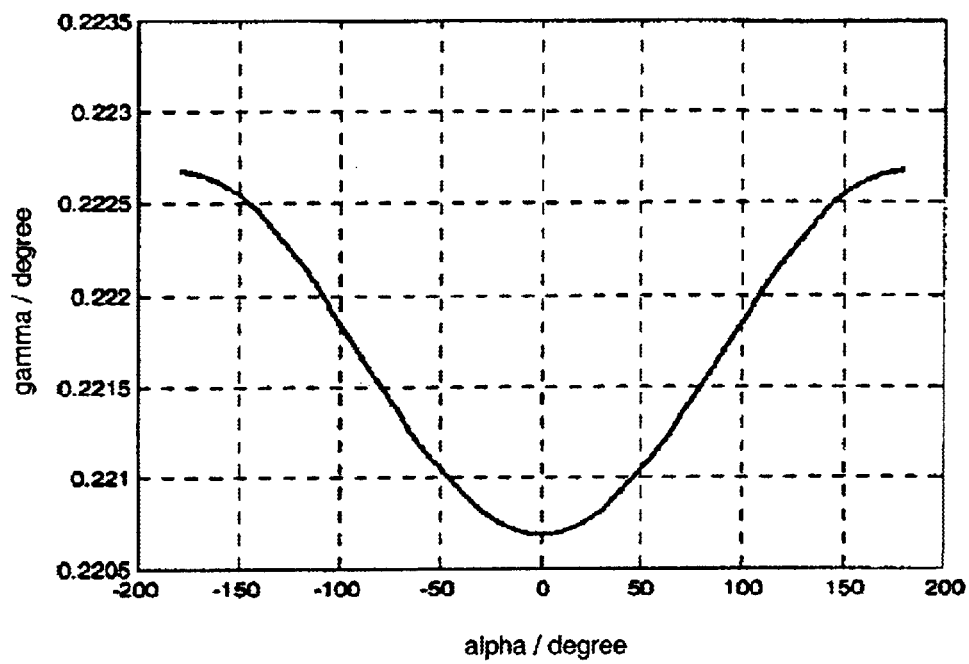
FIG. 19 shows the course of the angle of inclination γ' for the case with the tilted gantry as a function of the reference projection angle $\alpha_r$, specifically where M=16, p=16, and the gantry angle is ρ=30°.

As FIG. 19 shows, the angle of inclination γ' for the case of the tilted gantry is virtually independent of the reference projection angle $\alpha_r$. FIG. 19 shows the situation for a number of rows M=16, a pitch p=16, and a gantry angle of ρ=30°.

Figure 20:
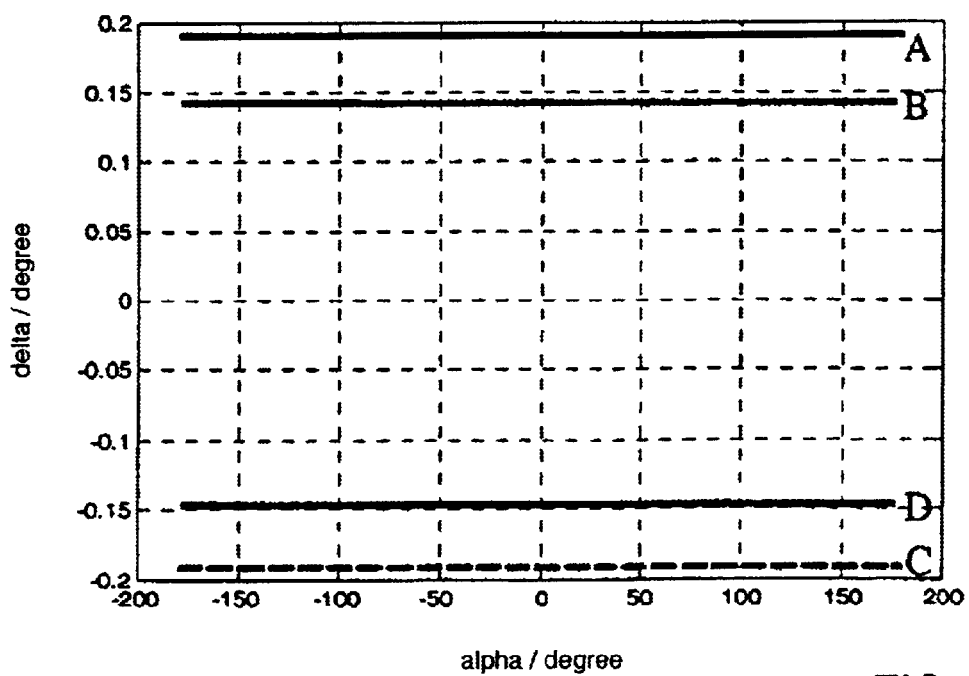
FIG. 20 shows the course of the maximum tilt angle $\delta_{max}$ for the case with the tilted gantry as a function of the reference projection angle $\alpha_r$, where M=16, p=16, and specifically where ρ=30°, ρ=0°, and ±RFOV.

The maximum tilt angle $\delta_{max}$ is also, as FIG. 20 shows, virtually independent of the reference projection angle $\alpha_r$; FIG. 20 also shows the situation where the number of rows is M=16, the pitch is p=16, and the gantry angle is ρ=30°. Here, A shows the course of the maximum tilt angle $\delta_{max}$ for +RFOV and ρ=30°, while C shows the course of the maximum angle of inclination for −RFOV and ρ=30°.

For comparison, in FIG. 20 the corresponding courses of the maximum tilt angle $\delta_{max}$ are plotted for a gantry angle of ρ=0°; B applies to +RFOV and ρ=0°, while D applies to −RFOV and ρ=0°.

Figure 21:
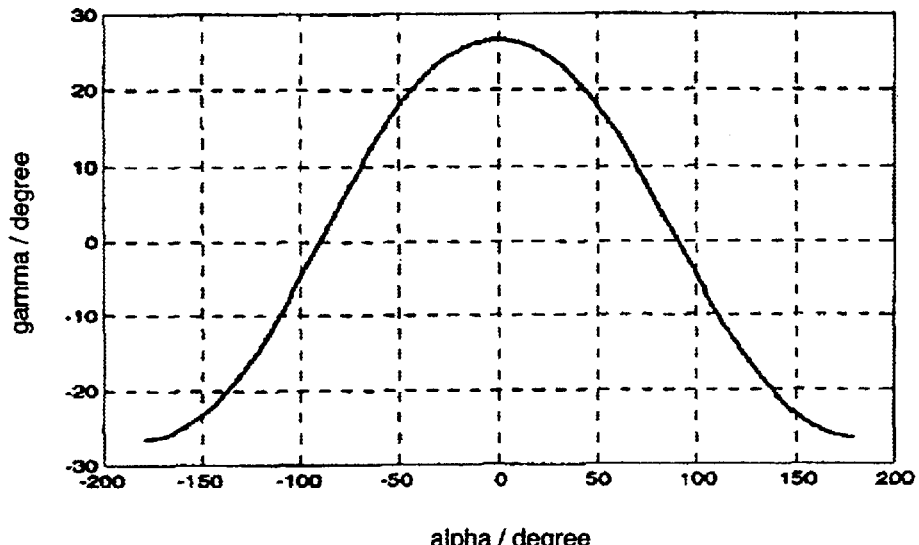
FIG. 21 is an illustration analogous to FIG. 19, but for a CT apparatus of the prior art.

To illustrate the effect of the invention, in FIG. 21, analogously to FIG. 19, the course of the angle of inclination y is shown as a function of the reference projection angle, again for a number of rows of M=16, a pitch of p=16, and a gantry angle of ρ=30°, for the method known from U.S. Pat. No. 5,802,134. It becomes clear that in this case there is a strong dependency of the angle of inclination γ on the reference projection angle $\alpha_r$.

FIGS. 19–21 furthermore each show one fill revolution (360°) of the focal point F.

In the case of the inclined gantry as well, for a given amount of the maximum value of the tilt angle $|\delta_{max}|$, which is obtained for instance from equation (10) on the basis of the inclination according to equation (21), the possibility exists of ascertaining the associated optimal value of the angle of inclination γ' from the slope of the spiral path H in such a way that an error criterion, such as a minimum mean value of the distances, measured in the z-direction, of all the points on the spiral segment from the image plane is met.

In summary, it can be stated that the spiral path is divided into overlapping spiral segments whose minimum length is scan $\alpha_{scan}$, $\geq\pi$, and that for each of these segments, one booklet with $N_{tilt}$ doubly inclined pages are ascertained, which are combined into one booklet. Accordingly, one booklet is unambiguously assigned one spiral segment whose center is defined by the reference projection angle $\alpha_r$. For each of the spiral segments, the pages for the $N_{tilt}$ different image inclinations, and optionally also different spiral revolutions, are reformatted as described to a particular desired target image planes of uniform orientation (for instance by device of a weighting method).

Figure 22:
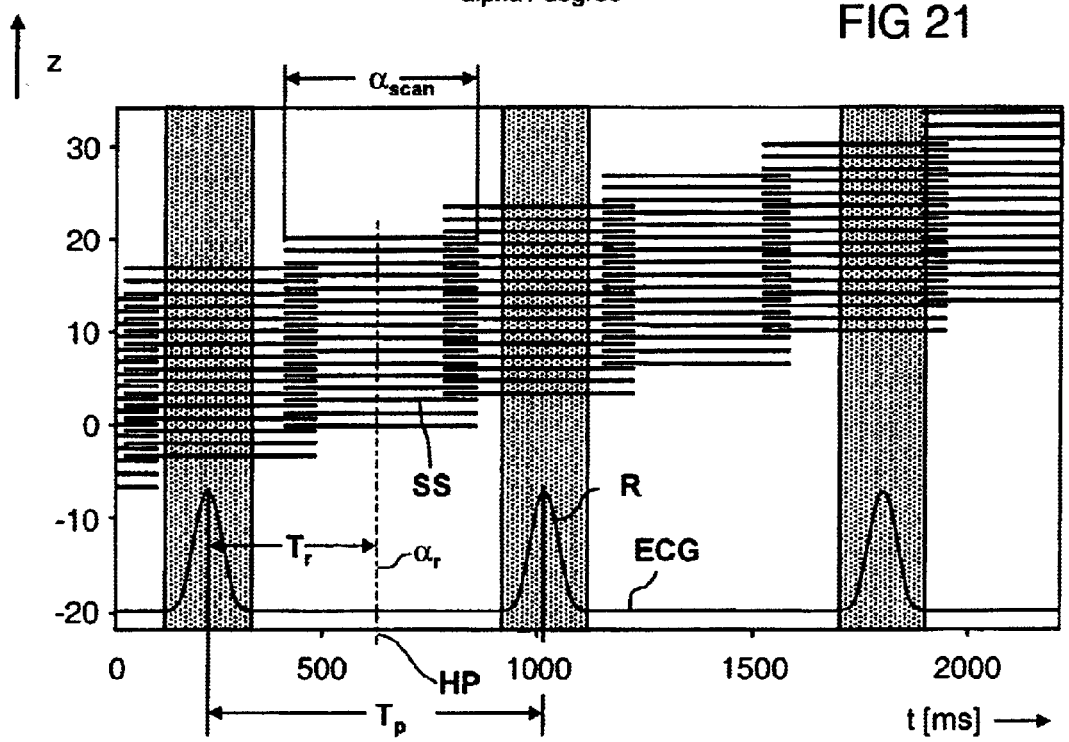
FIGS. 22 and 23 show various graphs illustrating acquisition, together with the recording of an EKG, for three different types of operation.

In FIG. 22, over the time t and thus—because of the constant speed of rotation of the gantry—over the projection angle α, on the one hand for one detector row, the positions of the pages of the booklets corresponding to the individual spiral segments, one of which is marked SS, are shown in the z-direction, and on the other, the course over time, marked ECG, of the EKG signal is shown. The pages are shown in the form of a stack of lines extending parallel to the t-axis.

The period length of one cardiac cycle, defined by two successive R waves in the EKG, which are marked R, is marked $T_p$ in FIG. 22. The phases of motion of the cardiac cycles that are generally not suitable for imaging are within the range of the respective R wave and are shaded in FIG. 22.

Since parallel to the continuous scanning of the patient P, his EKG is being recorded, an ambiguous association of the chronological positions in the EKG with the reference projection angles $\alpha_r$ of the booklets exists. For the spiral segment marked SS, the reference projection angle $\alpha_r$ in FIG. 22 is indicated by a dot-dashed line. It is thus possible, in a first EKG-based type of operation, to incorporate only booklets selected with a correct phase in terms of cardiac activity to be included into the above-described image reconstruction and image reformatting, as becomes clear from the first EKG-based type of operation shown in FIG. 22; the desired cardiac phase is marked HP, is offset by $T_r$ from the previous R wave, and in the case of the situation shown in FIG. 22, matches the reference projection angle.

The chronological resolution $\Delta t$ attainable in the first EKG-based type of operation amounts to at least:

$$\Delta t = \frac{\alpha_{scan}}{2\pi} T_{rot}$$

in which $T_{rot}$ designates the rotation time of the CT apparatus, that is, the time taken by one complete revolution of the gantry.

For gapless scanning of the region of interest of the object being examined, the slope of the spiral path is under some circumstances theoretically limited. In order nevertheless to make sufficiently great slopes of the spiral path possible, the following provisions are possible:

Booklets immediately adjacent to the selected cardiac phase, which are chronologically associated with the resting phase of the heart, can likewise be used for the reformatting. This increases the target volume that can be reconstructed per cardiac cycle.

Pages with a maximum angle of inclination can be reformed with an increased interpolation width.

At extremely low heart rates (if premature contractions are present), slices that because of excessive spiral advancement cannot be reformatted can be calculated by interpolative methods.

To enhance the chronological resolution, in two further EKG-based types of operation, the pages are reconstructed or reformatted on the basis of a spiral segment that is composed of output data that originate in a plurality of cardiac cycles, preferably cardiac cycles that immediately succeed one another, to which end the spiral segment of length $\alpha_{scan}$ required for the reconstruction is subdivided into a plurality of subsegments that add up in complementary fashion to make the spiral segment.

This subdivision will now be described, in conjunction with FIGS. 23 and 24 which are similar to FIG. 22 in their form of illustration, for the case where the spiral segments are each subdivided into two subsegments US1 and US2; a subdivision into more than two subsegments is also possible.

Figure 23:
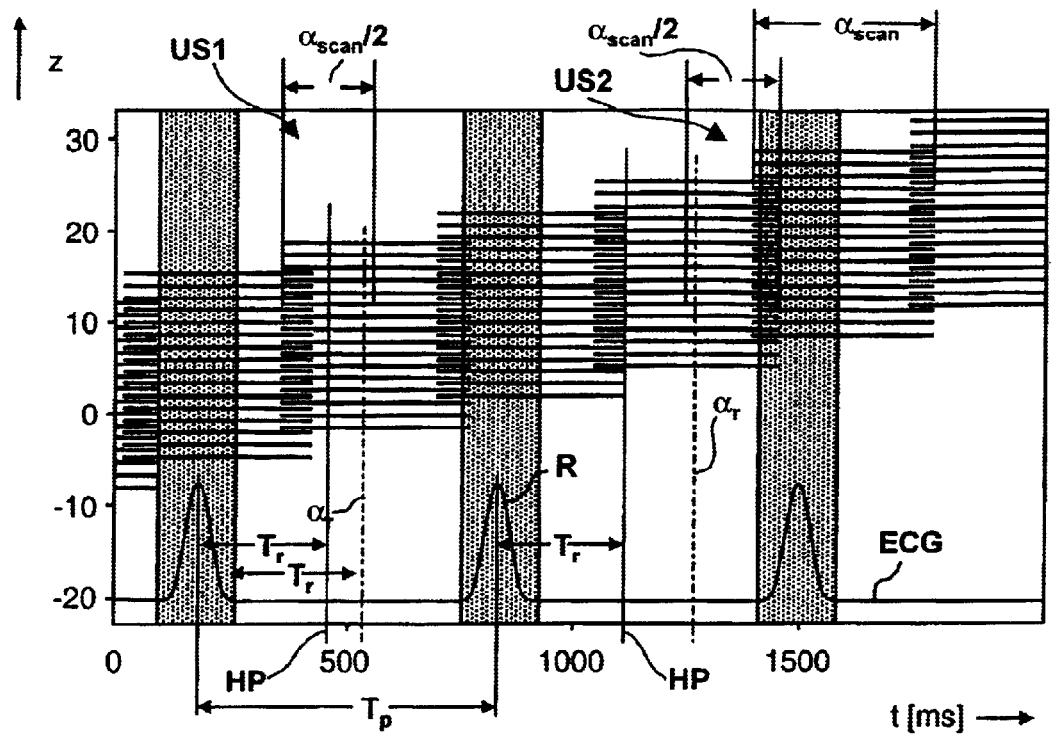

In the first of these two EKG-based types of operation, as shown in FIG. 23, a subdivision into two subsegments US1 and US2 of the same length $\alpha_{scan}/2$ is made.

In the first of the two cardiac cycles used, the subsegment US1 of length $\alpha_{scan}/2$ is determined in phase with the desired cardiac phase marked HP. In the second, ensuing heart cycle, a subsegment US2 of length $\alpha_{scan}/2$ is determined, which in complementary fashion supplements the subsegment US1 to make one data interval, that is, one spiral segment, of length $\alpha_{scan}$, and which has the least chronological spacing from the desired cardiac phase HP of the second cardiac cycle.

Since each cardiac cycle can be said to be involved in the buildup of two successive partial volumes, yet the chronological positions of the corresponding fractional segments will in general be different, two booklets are determined per cardiac cycle. To build up the respective image volume, the booklets associated with the data segments are reconstructed and reformatted, as described, and then added up slice by slice to make one complete CT image.

The chronological resolution is dependent on the local heart rate, and in the most favorable case, with a precisely in-phase location of the two sectors, it is:

$$\Delta t = \frac{\alpha_{scan}}{4\pi} T_{rot}$$

, im ungunstigsten Fall $$\Delta t = \frac{\alpha_{scan}}{2\pi} T_{rot}$$

while in the least favorable case it is:

In view of the fact that during an examination the heart rate of the patient may fluctuate, the term of the heart rate which was present when the particular output data in question were acquired is obtained from the local heart rate device. The local heart rate can readily be learned from the EKG signal, since it is obtained from the period length of the cardiac cycle at the time the output data in question are picked up.

Figure 24:
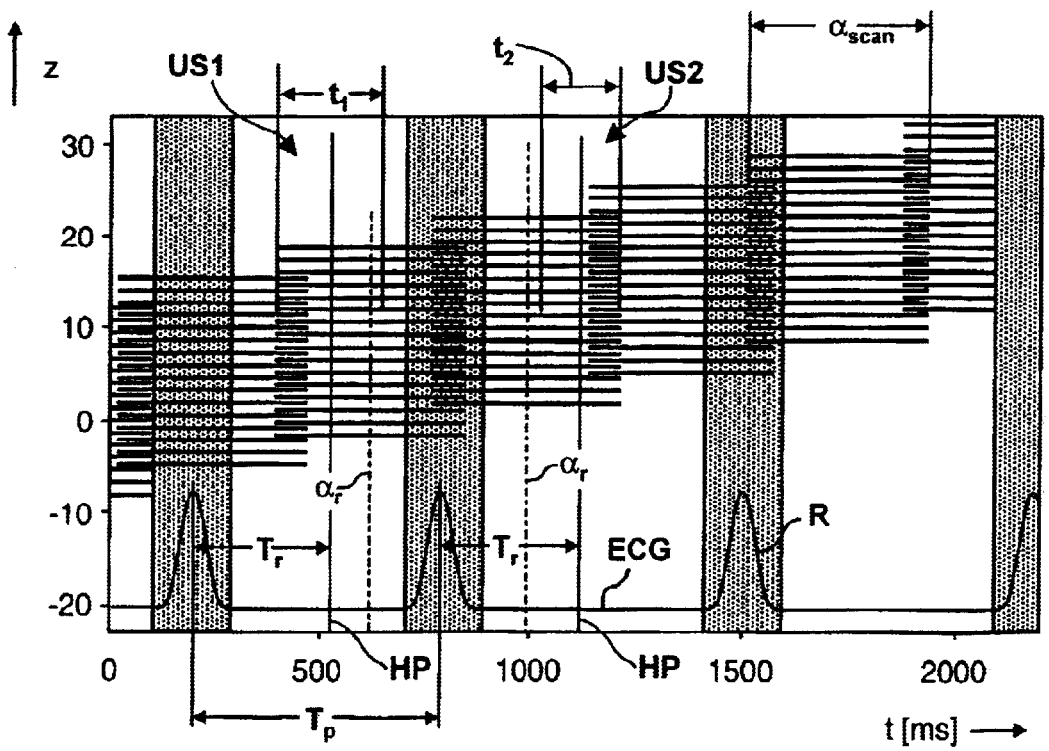

In the second of the two EKG-based types of operation based on a subdivision, in FIG. 24 a subdivision is made into two subsegments US1 and US2 of different length.

The subsegments US1 and US2 are determined such that they add up in complementary fashion to make one spiral segment of length $\alpha_{scan}$, but their chronological position in the successive cardiac cycles is exactly in-phase with, that is, symmetrical to, the desired cardiac phase HP. As a rule, the result is segments US1 and US2 of different length $t_1$ and $t_2$, respectively.

Once again, two cardiac cycles are required to build up one partial volume. Since the lengths of the subsegments US1 and US2 of the $i^{th}$ partial volume depend in general on the local heart rate at the time of the definitive subsegments US1 and US2 and therefore on the index i, it is necessary to calculate two booklets of different segment length in each cardiac cycle.

As noted, each cardiac cycle is involved in the buildup of two successive partial volumes. To build up the respective image volume, the booklets associated with the spiral segments are reconstructed and reformatted, and after that they are added up in slices to make one complete CT image.

The chronological resolution is dependent on the local heart rate and in the most favorable case, because of the equal length of the two subsegments US1 and US2, it is $$\Delta t = \frac{\alpha_{scan}}{4\pi} T_{rot}$$

, im ungunstugsten Fall $$\Delta t = \frac{\alpha_{scan}}{2\pi} T_{rot}$$

and in the least favorable case, that is, one of the two subsegments has the length of zero, which is the limit case for the type of operation of FIG. 22.

A reference time in the EKG that corresponds to the particular desired cardiac phase HP can be defined by providing that it is assigned a chronological spacing, marked $T_r$ in FIGS. 23 and 24, from the respective preceding R wave, this spacing characterizing the desired cardiac phase HP; in view of fluctuations in the heart rate, this chronological spacing is equivalent to an adjustable fraction of the period length of the particular current cardiac cycle. Instead of the current period length, a period length that is averaged over an adjustable number of preceding cardiac cycles can be used.

If an x-ray tube is used as the x-ray source 2, then in a manner known per se, by reducing the tube current during the contraction phase of the heart, when no image calculation is to be done, the dose applied to the patient can be reduced. To that end, the control unit 18 triggers the generator unit 17 accordingly on the basis of the EKG signal.

The layout of the image computer 11, in the case of the above exemplary embodiment, is described as if the preprocessing unit 12 and the reconstruction unit 13 were hardware components. This can in fact be the case. As a rule, however, these components are realized by software modules, which run an a universal computer provided with the requisite interfaces; in a departure from FIG. 1, this computer can also take on the function of the control unit 18, which them becomes superfluous.

The CT apparatus, in the case of the exemplary embodiment described, has a detector array 5 with rows, whose width measured in the z-direction is equal and amounts for instance to 1 mm. In a departure from this, a detector array whose rows are of different widths can also be provided within the scope of the invention. For instance, two inner rows each 1 mm wide and on either side of them each a respective row 2 mm can be provided.

In the case of the exemplary embodiments described, the relative motion between the measuring unit 1 and the support device 9 can be generated in each case by displacement of the support device 9. However, within the scope of the invention, it is also possible to keep the support device 9 stationary and instead to displace the measuring unit 1. Moreover, within the scope of the invention, the possibility exists of generating the requisite relative motion by displacing both the measuring unit and the support device 9.

In connection with the exemplary embodiments described above, third-generation CT apparatuses are used; that is, the x-ray source and the detector array are shifted jointly about the system axis during the imaging process. However, the invention can also be used in conjunction with CT apparatuses of the fourth generation, in which only the x-ray source is shifted about the system axis and cooperates with a fixed detector ring, as long as the detector array is a generally flat or two-dimensional array of detector elements.

In fifth-generation CT apparatuses as well, that is, those in which the x-radiation originates not merely at a focal point but rather at multiple focal points of one or more x-ray sources shifted about the system axis, the method of the invention can be used, as long as the detector array has a generally flat array of detector elements.

The CT apparatuses used in conjunction with the exemplary embodiments described above have a detector array with detector elements arranged on the order of an orthogonal matrix. However, the invention can also be employed in conjunction with CT apparatuses whose detector array has detector elements arranged in some other way as a generally flat array.

The invention is suitable not only for examining the heart but also for examining other regions that are periodically moved, for instance as a result of respiration activity on the part of the patient; a suitable sensor for detecting the particular kind of periodic motion should be provided.

The exemplary embodiments described above pertain to medical use of the method of the invention. However, the invention can also be employed outside the field of medicine.

What is claimed is:

1. A method for performing computed tomography, the method comprising:
   a) for scanning an object by a cone-shaped beam exiting from a focal point and by a matrix-like detector array for detecting the beam, the focal point is moved in relation to the object on a spiral path about a system axis, and the detector array provides output data corresponding to the received radiation; and
   b) for imaging an object region that executes a periodic motion, a signal that reproduces the course over time of the periodic motion is obtained during the scanning;
   c) from output data furnished during the motion of the focal point on a spiral segment, images with an inclined image plane are reconstructed, the image planes being inclined relative to the system axis both by an angle of inclination γ about a first axis which perpendicularly intersects the system axis, and by a tilt angle δ about a second axis which perpendicularly intersects both the first axis and the system axis; and spiral segments that succeed one another overlap one another by an overlap angle that is greater than or equal to zero; and the spiral segments are selected, taking into account the signal that reproduces the course over time of the periodic motion, such that they correspond to a phase of the periodic motion that is to be imaged.

2. The method of claim 1 in which the images with an inclined image plane are reconstructed from output data that belong to a spiral segment which originates in a single cycle of the periodic motion.

3. The method of claim 1 in which the images with an inclined image plane from a spiral segment comprising output data that originates in a plurality of cycles of the periodic motion are reconstructed.

4. The method of claim 3 in which the output data of which the spiral segment comprises originates in cycles of the periodic motion that immediately succeed one another.

5. The method of claim 3 in which the output data of which the spiral segment comprises originates in subsegments of equal length.

6. The method of claim 3 in which the output data of which the spiral segment comprises originates in subsegments of unequal length, each of which is disposed symmetrically to a reference time of the periodic motion.

7. The method of claim 6 in which the reference time in each case is later than the onset of one period of the periodic motion, by a length of time that is equivalent to an adjustable fraction of the period length of the periodic motion.

8. The method of claim 7 in which the reference time in each case is later than the onset of one period of the periodic motion, by a length of time that is equivalent to an adjustable fraction of the mean period length of the periodic motion.

9. The method of claim 1 in which for a number $n_{ima}$ of successive spiral segments, images with a respective inclined image plane are reconstructed, and the image planes have the same z-position $z_{ima}$, and spiral segments that immediately succeed one another are offset from one another by at most 180° and result in a total segment of length $[-\alpha_{max}, +\alpha_{max}]$, in which $\alpha_{max}=M\pi/p$, and M is the number of detector rows.

10. The method of claim 1 in which each spiral segment has a length of 180° plus cone angle, and in which for each spiral segment, images with an inclined image plane are reconstructed for a number $n_{ima}$ of inclined image planes, and the image planes have different z-positions $z_{ima}$.

11. The method of claim 10 in which the plurality of inclined image planes intersect at a straight line that extends at a tangent to the spiral.

12. The method of claim 10 in which, for the extreme values $+\delta_{max}$ and $-\delta_{max}$ of the tilt angle δ of the inclined image planes belonging to one spiral segment, the following equation applies:

$$\pm\delta_{max} = \arctan\left(\frac{-\frac{SM}{2} + Sp\frac{\alpha_1}{2\pi} \pm RFOV\cos\alpha_1\tan\gamma_0}{-\frac{R_f}{\cos\gamma_0} - (\pm RFOV)\frac{\sin\alpha_1}{\cos\gamma_0}}\right)$$

in which $\delta_0$ is the value, averaged for the tilt angle $\delta=0$ in accordance with the equation $$\gamma_0 = \tan\left(\frac{-Sp\hat{\alpha}}{2\pi R_f \sin\hat{\alpha}}\right)$$

of the angle of inclination $\gamma$.

13. The method of claim 1 in which the focal point rotates about an axis of rotation about the system axis.

14. The method of claim 1 in which the axis of rotation, about which the focal point rotates about the system axis, intersects the system axis at a gantry angle $\rho$, and for the angle of inclination $\gamma'$ to be selected, the following equation applies:

$$\gamma' = \arctan\frac{Sp \cdot \cos\rho}{\sqrt{4\pi^2 \cdot R_f + S^1 p^2 + 4\pi \cdot R_f \cos\alpha\sin\rho \cdot Sp}}.$$

15. The method of claim 12 in which for a given amount $|\delta_{max}|$ of the maximum value for the tilt angle $\delta$, the associated optimal value $\gamma_{min}$ of the angle of inclination $\gamma$ is ascertained such that an error criterion is met.

16. The method of claim 10 in which for the number $n_{ima}$ of inclined image planes for which images with an inclined image plane are generated for each spiral segment, the following equation applies:

$$n_{ima} = \text{floor}\left[\frac{sM}{p}\right].$$

17. The method of claim 16 in which the tilt angles $\delta$ of the inclined image planes are ascertained in accordance with the equation $$\delta(i) = \delta_{max}\frac{2i - (n_{ima} - 1)}{n_{ima} - 1}.$$

18. The method of claim 1 having the further method act that a transverse section image of a transverse slice, the latter intersecting the system axis at a right angle, is generated by combining a plurality of images with an inclined image plane.

19. The method of claim 18 in which the combination of the plurality of images with an inclined image plane to produce a transverse section image is effected by interpolation.

20. The method of claim 19 in which the combination of the plurality of images with an inclined image plane to produce a transverse section image is effected by averaging.

21. The method of claim 20 in which the combination of the plurality of images with an inclined image plane to generate a transverse section image is effected by weighted averaging.

22. The method of claim 18 which also has the method act that the number of images with an inclined image plane that are combined to generate a transverse section image is selected in accordance with whatever slice thickness of the transverse slice is desired.

23. The method of claim 22 in which the images with an inclined image plane having the least possible slice thickness are reconstructed.

24. The method of claim 22 in which the number of images with an inclined image plane that are combined to generate a transverse section image is selected in accordance with the equation $$N_M = 2 \cdot \max(z^*, \sup_\Phi \Delta z_R)/S \cdot N_S.$$

25. A computed tomography (CT) apparatus, having a radiation source from whose focal point a cone-shaped beam is emitted; having a matrix-like detector array for detecting the beam, the detector array providing output data corresponding to the received radiation; having a device for generating a relative motion between the radiation source and the detector array on the one hand and an object on the other; and having a computer, to which the output data are supplied, wherein the device for creating a relative motion for scanning the object by the beam and the two-dimensional detector array cause a relative motion of the focal point in respect to a system axis in such a way that the focal point moves on a path that is spiral in relation to the system axis; and for imaging an object region that executes a periodic motion, a device which during the scanning obtains a signal that reproduces the course over time of the periodic motion, and from the respective output data furnished during the motion of the focal spot on a spiral segment, the computer reconstructs images with an inclined image plane, the image planes being inclined relative to the system axis both by an angle of inclination $\gamma$ about a first axis which perpendicularly intersects the system axis, and by a tilt angle $\delta$ about a second axis which perpendicularly intersects both the first axis and the system axis; and spiral segments that immediately succeed one another overlap one another by an overlap angle that is greater than or equal to zero; and the spiral segments are selected, taking into account the signal that reproduces the course over time of the periodic motion, such that they correspond to a phase of the periodic motion that is to be imaged.

26. The CT apparatus of claim 25 in which the computer is operable to reconstruct the images with an inclined image plane from output data that belong to a spiral segment which originates in a single cycle of the periodic motion.

27. The CT apparatus of claim 25 in which the computer is operable to reconstruct the images with an inclined image plane from a spiral segment that comprises output data that originates in a plurality of cycles of the periodic motion.

28. The CT apparatus of claim 27 in which the output data of which the spiral segment comprises originates in cycles of the periodic motion that immediately succeed one another.

29. The CT apparatus of claim 27 in which the output data of which the spiral segment comprises originates in subsegments of equal length.

30. The CT apparatus of claim 27 in which the output data of which the spiral segment comprises originate in subsegments of unequal length, each of which is disposed symmetrically to a reference time of the periodic motion.

31. The CT apparatus of claim 30 in which the reference time in each case is later than the onset of one period of the periodic motion by a length of time that is equivalent to an adjustable fraction of the period length of the periodic motion.

32. The CT apparatus of claim 30 which the reference time in each case is later than the onset of one period of the periodic motion by a length of time that is about an adjustable fraction of the mean period length of the periodic motion.

33. The CT apparatus of claim 25 in which for a number $n_{ima}$ of successive spiral segments, the computer is operable to reconstruct images with an inclined image plane, and the image planes have the same z-position $z_{ima}$, and spiral segments that immediately succeed one another are offset from one another by at most 180° and result in a total segment of length $[-\alpha_{max}, +\alpha_{max}]$, in which $\alpha_{max}=M\pi/p$, and M is the number of detector rows.

34. The CT apparatus of claim 25 in which each spiral segment has a length of 180° plus cone angle, and in which for each spiral segment, the computer reconstructs images with an inclined image plane for a number $n_{ima}$ of inclined image planes, and the image planes have the different z-positions $z_{ima}$.

35. The CT apparatus of claim 34 in which the plurality of inclined image planes intersect at a straight line that extends at a tangent to the spiral.

36. The CT apparatus of claim 34 in which, for the extreme values $+\delta_{max}$ and $-\delta_{max}$ of the tilt angle $\delta$ of the inclined image planes belonging to one spiral segment, the following equation applies:

$$\pm\delta_{max} = \arctan\left(\frac{-\frac{SM}{2} + Sp\frac{\alpha_1}{2\pi} \pm RFOV\cos\alpha_1\tan\gamma_0}{-\frac{R_f}{\cos\gamma_0} - (\pm RFOV)\frac{\sin\alpha_1}{\cos\gamma_0}}\right)$$

in which $\delta_0$ is the value, averaged for the tilt angle $\delta=0$ in accordance with the equation $$\gamma_0 = \tan\left(\frac{-Sp\hat{\alpha}}{2\pi R_f \sin\hat{\alpha}}\right)$$

of the angle of inclination $\gamma$.

37. The CT apparatus of claim 25 in which the focal point rotates about an axis of rotation about the system axis.

38. The CT apparatus of claim 25 in which the axis of rotation, about which the focal point rotates about the system axis, intersects the system axis at a gantry angle $\rho$, and the computer selects the angle of inclination $\gamma'$ in accordance with the following equation:

$$\gamma' = \arctan\frac{Sp\cdot\cos\rho}{\sqrt{4\pi^2\cdot R_f + S^2p^2 + 4\pi\cdot R_f\cos\alpha\sin\rho\cdot Sp}}.$$

39. The CT apparatus of claim 36 in which for a given amount $|\delta_{max}|$ of the maximum value for the tilt angle $\delta$, the computer ascertains the associated optimal value $\gamma_{min}$ of the angle of inclination $\gamma$ is ascertained such that an error criterion is met.

40. The CT apparatus of claim 34 in which for the number $n_{ima}$ of inclined image planes for which the computer generates images with an inclined image plane for each spiral segment, the following equation applies:

$$n_{ima} = \text{floor}\left[\frac{sM}{p}\right].$$

41. The CT apparatus of claim 40 in which the computer is operable to ascertain the tilt angles $\delta$ of the inclined image planes in accordance with the equation $$\delta(i) = \delta_{max}\frac{2i - (n_{ima} - 1)}{n_{ima} - 1}.$$

42. The CT apparatus of claim 25 in which the computer is operable to generate a transverse section image of a transverse slice, the latter intersecting the system axis at a right angle, in that it combines a plurality of images with an inclined image plane.

43. The CT apparatus of claim 42 in which the computer is operable to accomplish the combination of the plurality of images with an inclined image plane to produce a transverse section image by interpolation.

44. The CT apparatus of claim 43 in which the computer is operable to accomplish the combination of the plurality of images with an inclined image plane to produce a transverse section image by averaging.

45. The CT apparatus of claim 44 in which the computer is operable to accomplish the combination of the plurality of images with an inclined image plane to generate a transverse section image by weighted averaging.

46. The CT apparatus of claims 42 in which the computer is operable to select the number of images with an inclined image plane that are combined to generate a transverse section image in accordance with whatever slice thickness of the transverse slice is desired.

47. The CT apparatus of claim 46 in which the computer is operable to reconstruct the images with an inclined image plane that have the least possible slice thickness.

48. The CT apparatus of claim 46 in which the computer is operable to select the number of images with an inclined image plane that are combined to generate a transverse section image, in accordance with the equation $$N_M = 2\cdot\max(z^*, \sup_\Phi \Delta z_R)/S\cdot N_S.$$

* * * * *